United States Patent [19]

Miller et al.

[11] Patent Number: 5,380,749
[45] Date of Patent: Jan. 10, 1995

[54] THIOXANTHENONE ANTITUMOR AGENTS

[75] Inventors: Theodore C. Miller; Joseph C. Collins, both of East Greenbush, N.Y.; Kenneth C. Mattes, Irondequoit; Mark P. Wentland, Colonie, both of N.Y.; Robert B. Perni, Robeson, Pa.; Thomas H. Corbett, Grosse Pointe Park, Mich.; Joseph W. Guiles, Chester Springs, Pa.

[73] Assignee: Sterling Winthrop Inc., New York, N.Y.

[21] Appl. No.: 216,989

[22] Filed: Mar. 23, 1994

Related U.S. Application Data

[60] Division of Ser. No. 44,843, Apr. 8, 1993, Pat. No. 5,346,917, which is a continuation-in-part of Ser. No. 835,159, Feb. 13, 1992, abandoned, which is a continuation-in-part of Ser. No. 713,173, Jun. 10, 1991, abandoned.

[51] Int. Cl.$^6$ .............. A61K 31/38; C07C 261/00; C07D 335/12; C07D 311/82
[52] U.S. Cl. ................. 514/437; 514/455; 560/24; 549/26; 549/27; 549/392
[58] Field of Search ............ 514/437, 455; 549/27, 549/26, 392; 560/24

[56] References Cited

U.S. PATENT DOCUMENTS

| | | | |
|---|---|---|---|
| 3,312,598 | 4/1967 | Rosi and Peruzotti | 435/117 |
| 3,745,172 | 7/1973 | Collins and Rossi | 549/27 |
| 4,539,412 | 9/1985 | Archer | 549/27 |
| 4,582,851 | 4/1986 | Worth | 514/437 |
| 4,737,514 | 4/1988 | Harfenist et al. | 514/437 |

OTHER PUBLICATIONS

I. Nabih & M. Elsheikh, "Chlorination and Condensation Reactions at the 4-Methyl Group of Lucanthone and Oxalucanthone", J. Pharm. Sci. 54, 1672-1673 (1965).

E. J. Blanz and F. A. French, "A Systematic Investigation of Thioxanthen-9-Ones and Analogs as Potential Antitumor Agents", J. Med. Chem. 6, 185-191 (1963).

A. Yarinsky & H. Freele, "A Comparison of Molluscicidal and Mollusc Inhibitory Activity of Hycanthone and Lucanthone and the Effect of the Drugs on the Development of Schistosoma mansoni in the Snail Intermediate Host, Australorbis glabratus," J. Tropical Med. Hyg. 73, 23-27 (1970).

B. Palmer et al., "Potential Antitumor Agents. 54. Chromophore Requirements for in Vivo Antitumor Activity among the General Class of Linear Tricyclic Carboxamides", J. Med. Chem. 31, 707-712 (1988).

Archer et al., J. Med. Chem. 31, 254-260 (1988).

Primary Examiner—Allen J. Robinson
Assistant Examiner—Deborah Lambkin
Attorney, Agent, or Firm—Michael D. Alexander; Paul E. Dupont

[57] ABSTRACT

1-[[(Dialkylamino)alkyl]amino]-4-substituted-thioxanthen-9-ones are disclosed as antitumor agents. Compositions containing the thioxanthenones and methods of treating tumors and cancer in mammals with the thioxanthenones are also disclosed.

55 Claims, No Drawings

THIOXANTHENONE ANTITUMOR AGENTS

CROSS REFERENCE TO RELATED APPLICATIONS

This application is a division of our prior copending application Ser. No. 08/044,843, filed Apr. 8, 1993, U.S. Pat. No. 5,346,917, which in turn is a continuation-in-part of our prior copending application Ser. No. 07/835,159, filed Feb. 13, 1992, now abandoned which in turn is a continuation-in-part of our prior copending application Ser. No. 07/713,173, filed Jun. 10, 1991, now abandoned.

FIELD OF THE INVENTION

The present invention relates to novel 1-[[(dialkylamino)alkyl]amino]-4-substituted-thioxanthen-9-ones, to pharmaceutical compositions containing the thioxanthenones, to methods of treating tumors with the thioxanthenones and to methods of treating cancer in mammals with the compositions containing the thioxanthenones.

INFORMATION DISCLOSURE STATEMENT

Nabih and Elsheikh [*J. Pharm. Sci.* 54, 1672-1673 (1965)] disclose 1- [[2-(diethylamino)ethyl]amino]-4-[(diethylamino)methyl ]thioxanthen-9-one. No utility was demonstrated for the compound.

Collins and Rosi U.S. Pat. No. 3,745,172 disclose as an intermediate in the synthesis of antifungal and antibacterial agents:

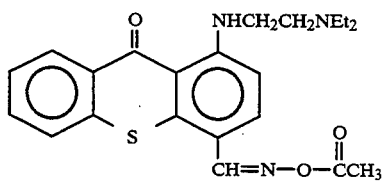

and as an anthelmintic and antibacterial agent:

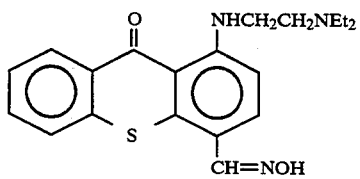

Rosi and Peruzotti U.S. Pat. No. 3,312,598 disclose 1-[[2-(diethylamino)ethyl]amino]-9-oxo-9H-thioxanthene-4-carboxylic acid as a by-product of fermentation having no disclosed utility.

Blanz and French [*J. Med. Chem.* 6, 185-191 (1963)] disclose the synthesis of a series of thioxanthenones related to lucanthone and the results of the testing of the compounds against a leukemia and two solid tumors. Among the compounds disclosed are

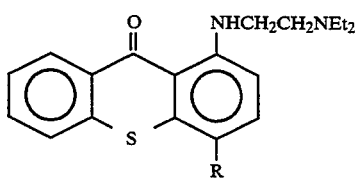

wherein R is methyl, methoxyl, and ethoxyl.

Yarinsky and Freele [Journal of Tropical Medicine and Hygiene 73, 23-27 (1970)] disclose

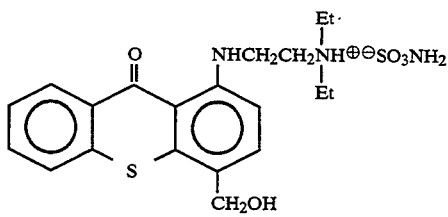

as an antischistosomal agent.

Palmer et al. [*J. Med. Chem.* 31, 707-712 (1988)] disclose N-[2-(dimethylamino)ethyl]-9-oxo-9H-thioxanthene-4-carboxamide monohydrochloride which was tested in vitro versus murine leukemia (L1210) and in vivo versus P388 leukemia cells and was found to be "unlikely to be worth pursuing" as a potential antitumor agent.

Archer, U.S. Pat. No. 4,539,412, issued Sep. 3, 1985, discloses compounds of the formula:

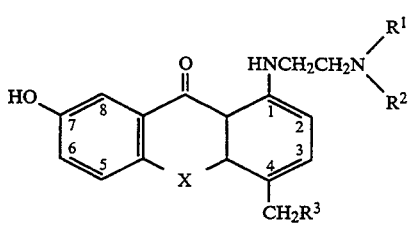

wherein, for X=S:
  $R^1$ and $R^2$ are individually selected from one of lower-alkyls, and jointly selected to form one of pyrrolidinyl, piperidinyl, morpholinyl, piperazinyl and N-substituted piperazinyl; and
  $R^3$ is H or hydroxy.
Where X=O:
  $R^1$ and $R^2$ are individually selected from one of lower-alkyls, and jointly selected from one of pyrrolidinyl, piperidyl, morpholinyl, piperazinyl and N-substituted piperazinyl; and
  $R^3$ is hydroxy.

The compounds are said to be useful as antitumor agents.

Archer et al. [*J. Med. Chem.* 31, 254-260 (1988)] disclose compounds of the general formula:

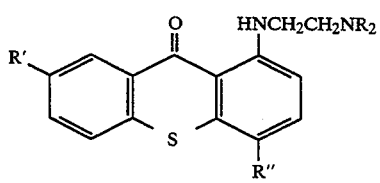

wherein R=$C_2H_5$, R'=H, R"=$CH_2OH$ (example 1); R=$CH_3$, R'=OH, R"=$CH_2OH$ (example 2); R=$C_2H_5$, R'=H, R"=$CH_2OCONHCH_3$ (example 4); R=$CH_3$, R'=OH, R"=$CH_2OCONHCH_3$ (example 5); R=$C_2H_5$, R'=H, R"=$CH_2OCONHC_6H_5$ (example 23); R=$C_2H_5$; R'=H, R"=$CH_2OCONHC_3H_7$ (example 24); R=$C_2H_5$, R'=H, R"=$CH_2OCONHC_4H_9$ (example 25); R=$C_2H_5$, R'=H, R"=$CH_2OCOOCH_3$ (example 26); R=$C_2H_5$, R'=H, R"=$CH_2OCOCH_3$ (example 27) or R=C₂H₅, R'=H, R"=CH₂OCOC₆H₃ (NO₂)₂ (example 28) and the results of the testing of these compounds for antitumor and/or antischistosomicidal activity.

SUMMARY OF THE INVENTION

In a product aspect the invention relates to compounds of the formula I

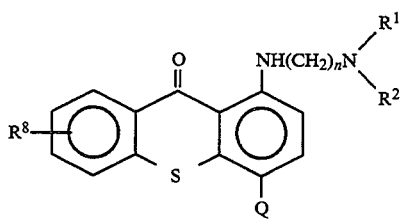

wherein n is 2 or 3;

$R^1$ and $R^2$ are independently lower-alkyl;

Q is a residue chosen from the group consisting of $CH_2NHR^3$, $CH_2N(R^4)SO_2R^7$, $CH_2NHCHO$, $CH=N-Ar$ $C(O)NR^5R^6$, $CH_2N(R^4)C-(O)R^7$, $CH_2N(C_2H_5)CHO$, $CH_2N(R^4)P(O)$ (O-lower-alkyl)₂, $CH_2N=CH-N$ $(R^9)$ $(R^{10})$, $CH_2N(R^4)C(O)CF_3$ and $CH_2N(R^4)C(O)OR^7$;

$R^3$ is hydrogen or lower-alkyl;

$R^4$ is hydrogen, lower-alkyl or Ar;

$R^5$ is hydrogen, lower-alkyl or Ar;

$R^6$ is hydrogen or lower-alkyl;

$R^7$ is lower-alkyl, or Ar;

$R^8$ is hydrogen, lower-alkyl, lower-alkoxy, or hydroxy;

Ar is phenyl or phenyl substituted with methyl, methoxyl, hydroxy, halogen or nitro, with the proviso that when n is 2, $R^1$ and $R^2$ are ethyl, $R^8$ is hydrogen and Q is $CH_2NHSO_2Ar$, the Ar group cannot be 4-monosubstituted by methyl or halogen; and $R^9$ and $R^{10}$ are independently lower-alkyl;

or a pharmaceutically acceptable acid-addition salt or solvate thereof. The compounds are useful for the treatment of tumors in mammals.

Among the compounds within the ambit of Formula I above are those wherein n is two or three, preferably two; $R^1$ and $R^2$ are independently lower-alkyl, preferably both are ethyl; Q is a residue chosen from the group consisting of $-CH_2NHR^3$, $-CH_2N(R^4)SO_2R^7$, $-CH_2NHCHO$, $-CH=N-Ar$, $-C(O)NR^5R^6$, $CH_2N(R^4)C(O)R^7$, $CH_2N(C_2H_5)CHO$, and $CH_2N(R^4)P(O)$ (O-lower-alkyl)₂; $R^3$ is hydrogen or lower-alkyl; $R^4$ is hydrogen or lower-alkyl; $R^5$ is hydrogen, lower-alkyl, or At, preferably hydrogen; $R^6$ is hydrogen or lower-alkyl, preferably hydrogen; $R^7$ is lower-alkyl, preferably methyl, or Ar; $R^8$ is hydrogen, lower-alkyl or lower-alkoxy; and Ar is phenyl or phenyl substituted with methyl, methoxyl, halogen or nitro with the proviso that when n is 2, $R^1$ and $R^2$ are ethyl, $R^8$ is hydrogen and Q is $CH_2NHSO_2Ar$, the Ar group cannot be 4-monosubstituted by methyl or halogen. Ar is preferably phenyl.

Lower-alkyl as used herein describes linear, branched or cyclic hydrocarbons containing four or fewer carbon atoms. Halogen describes bromine, chlorine or fluorine. The term lower-alkoxy means linear or branched alkyloxy substituents having from one to about four carbon atoms, for example, methoxy, ethoxy, propoxy, isopropoxy, butoxy, sec-butoxy, and the like.

In a further product aspect the invention relates to compositions for treating tumors and cancer in mammals which comprise compounds of formula I together with pharmaceutically acceptable excipients or diluents.

In a process aspect the invention relates to a method for treating tumors in mammals which comprises administering to the mammal a compound of formula I.

In a further process aspect the invention relates to a method for treating cancer in a mammal which comprises administering to the mammal a composition of a compound of formula I together with pharmaceutically acceptable excipients or diluents.

DETAILED DESCRIPTION INCLUSIVE OF PREFERRED EMBODIMENTS

The synthesis of compounds of the invention may be outlined as shown in Schemes A, B and C:

SCHEME A

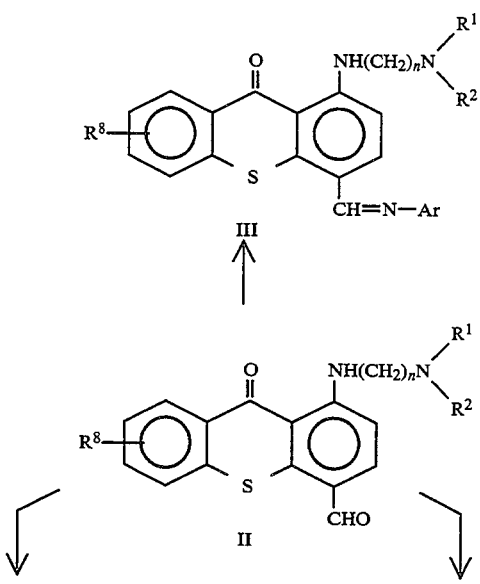

SCHEME A

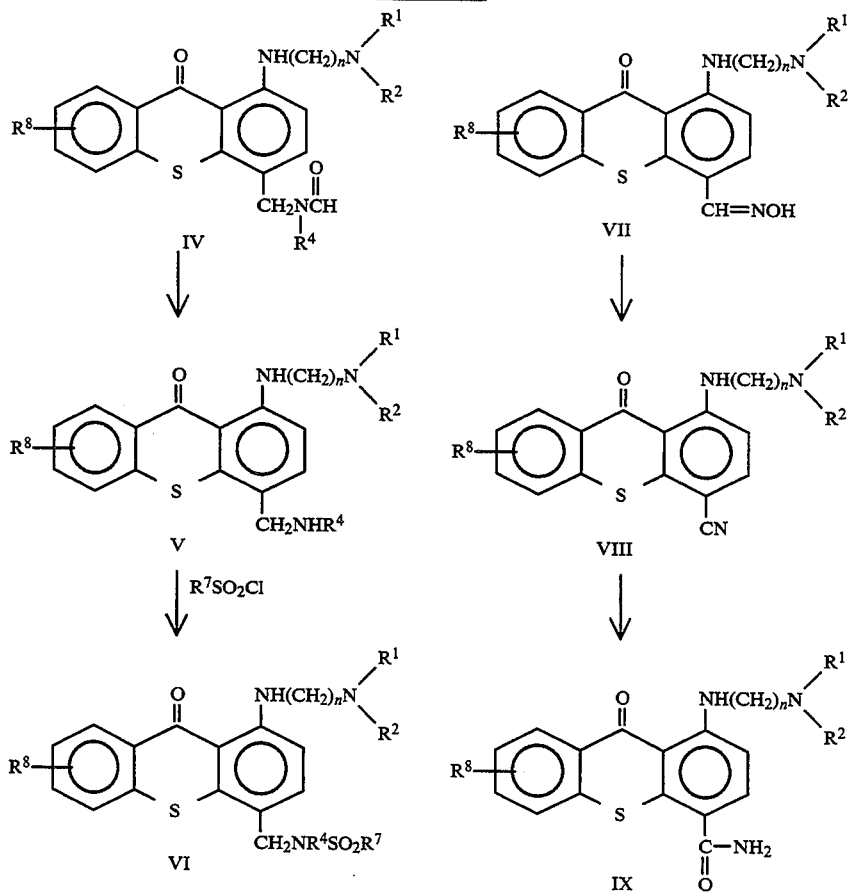

Scheme B

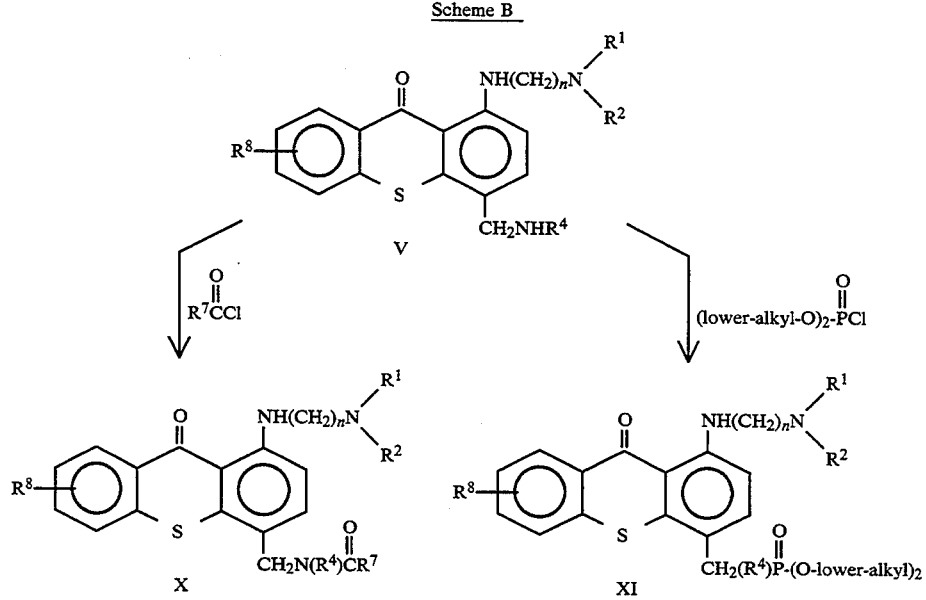

The compounds of formula III (formula I wherein Q is —CH=N—Ar) may be synthesized by heating an aldehyde of formula II together with about one equivalent of the appropriate aniline in an inert, azeotroping solvent, preferably xylene or toluene at reflux.

The compounds of formula IV may be prepared from an aldehyde of formula II by heating at 150° to 185° C. in the presence of from about 5 to about 17 equivalents of formic acid in formamide, N-alkylformamide or N-Ar-formamide as a solvent. The conditions are well known in the art for the Leuckart reaction. The compounds of formula V are then obtained by acid hydrolysis of the formamide.

The compounds of formula VI (formula I wherein Q is —CH$_2$N(R$^4$)SO$_2$R$^7$) may be synthesized by sulfonylation of the amine V with a slight excess of a lower-alkylsulfonyl, or arylsulfonyl chloride in (a) a suitable solvent, preferably pyridine, at 0° to 50° C.; or (b) a suitable solvent, such as dichloromethane, in the presence of an excess of a base, such as triethylamine, at a temperature in the range of about 0° C. up to about room temperature.

Alternatively, the compounds of formula VI, wherein R$^4$ is lower-alkyl, may be synthesized by sulfonylation of the amine V, wherein R$^4$ is hydrogen, as described above, followed by treatment of the resulting sulfonamide VI, R$^4$ is hydrogen, with an excess of a base, preferably sodium hydride, in a suitable solvent, such as tetrahydrofuran or N,N-dimethylformamide, followed by treatment with an excess of an appropriate lower-alkyl halide at a temperature in the range of about 0° C. up to the boiling point of the solvent used.

The carboxamides of formula IX may be synthesized by reacting the aldehyde II with a 5–6 fold excess of hydroxylamine hydrochloride in pyridine, optionally containing a cosolvent, followed by dehydration of the oxime (VII) by treating with an excess of acetic anhydride and heating in an inert, high-boiling solvent such as xylene, and, finally, partial hydrolysis of the nitrile (VIII) in concentrated sulfuric acid. In the cases where it is desired that R$^5$ and R$^6$ be other than hydrogen, the amide IX may be further hydrolyzed to the corresponding acid in 16% alcoholic KOH and the acid may be condensed with the appropriate amine using procedures well known in the art.

The compounds of formula X (formula I wherein Q is CH$_2$N(R$^4$)C(O)R$^7$) may be synthesized by acylation of the amine V with an excess of a lower-alkyl acid chloride, or aryl acid chloride in a suitable solvent, preferably pyridine, optionally in the presence of a cosolvent, preferably dichloromethane, at a temperature in the range from about 0° C. to about 50° C.

The compounds of formula XI (formula I wherein Q is CH$_2$N(R$^4$)P(O)(O-lower-alkyl)$_2$) may be synthesized by treatment of the amine V with an excess of an appropriate di-lower-alkyl phosphorochloridate in a suitable solvent, such as dichloromethane, in the presence of an excess of a base, preferably triethylamine, at a temperature in the range of from about 0° C. up to about 50° C.

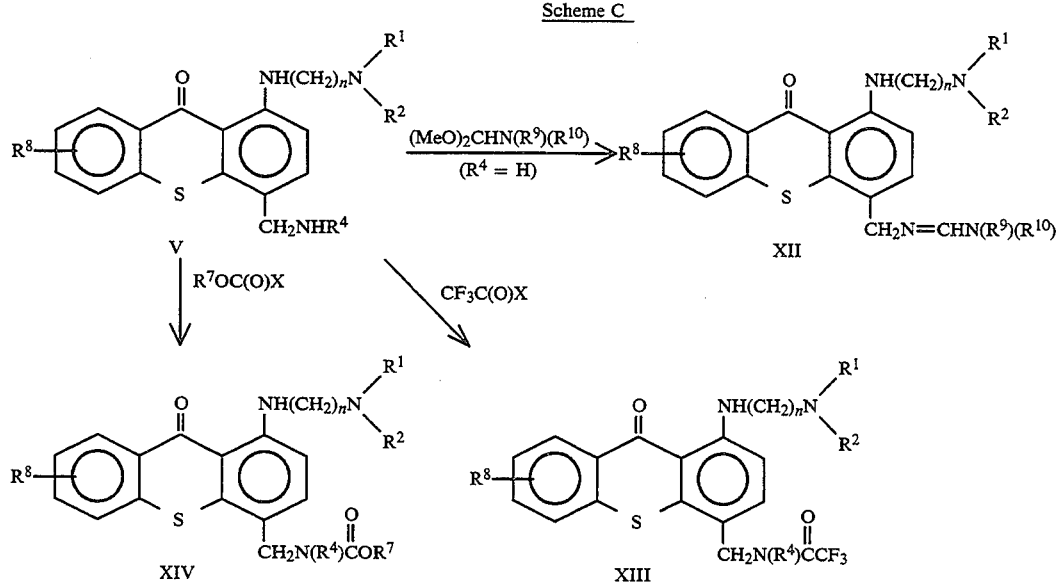

Scheme C

The compounds of formula XII (formula I wherein Q is CH$_2$N=CHN(R$^9$)(R$^{10}$)) may be synthesized by the treatment of the amine of formula V with an excess of a dimethyl acetal of formula (MeO)$_2$CHN(R$^9$)(R$^{10}$), at a temperature of about 60° C.

The compounds of formula XIII (formula I wherein Q is CH$_2$N(R$^4$)C(O)CF$_3$) may be synthesized by treatment of the amine V, in a suitable solvent, preferably dichloromethane, with an excess of a solution of a trifluoroacetyl halide of formula CF$_3$C(O)X wherein X is halogen, preferably trifluoroacetyl chloride, in a suitable solvent, preferably toluene, at a temperature of about 0° C.

The compounds of formula XIV (formula I wherein Q is CH$_2$N(R$^4$)C(O)OR$^7$) may be synthesized by treatment of the amine V with an excess of an appropriate haloformate of formula R$^7$OC(O)X wherein X is halogen, preferably chlorine, in the presence of an excess of a base, preferably triethylamine, in a suitable solvent, such as dichloromethane or chloroform, at a temperature in the range of about 0° C. up to about room temperature.

The aldehyde II is available by the method disclosed in U.S. Pat. No. 3,294,803, by MnO$_2$ oxidation of the alcohol obtained by the method of U.S. Pat. No. 3,711,512, or by the methods described hereinafter in the examples.

Simple chemical transformations which are conventional and well known to those skilled in the art of chemistry can be used for effecting changes in the functional groups of the compounds of the invention. For example, dealkylation of lower-alkyl aryl ethers to produce the corresponding phenol derivatives.

The compounds of formula I are useful both in the free base form and in the form of acid-addition salts, and both forms are within the purview of the invention. The acid-addition salts are in some cases a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. In practicing the present invention it is convenient to form the hydrochloride, fumarate, toluenesulfonate, methanesulfonate, or maleate salts. However, other appropriate medicinally acceptable salts within the scope of the invention are those derived from other mineral acids and organic acids. The acid-addition salts of the basic compounds are prepared either by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinal acceptable salt by ion exchange procedures.

The structures of the compounds of the invention were established by the mode of synthesis and by one or more of elemental analysis, and infrared, ultraviolet and nuclear magnetic resonance spectroscopy. The course of the reactions and the identity and homogeneity of the products were assessed by thin layer chromatography (TLC) or gas-liquid chromatography (GLC). The melting points are given in degrees C and are uncorrected. The starting materials are either commercially available or may be prepared by procedures well known in the art.

EXAMPLE 1

1-[[2-(Diethylamino)ethyl]amino]-4-(N-phenylformimidoyl) thioxanthen-9-one (I: $R^1=R^2=Et$; $Q=CH=N-C_6H_5$; $R^8=H$; n=2)

A mixture of 17.7 g (50 mmol) of 1-[[2-(diethylamino)ethyl]amino]-9-oxo-thioxanthen-4-carboxyaldehyde and 15.1 g (150 mmol) of aniline in 100 mL of toluene was refluxed for 8 hours with a Dean-Stark trap. TLC on alumina with chloroform/hexane/isopropylamine 10:10:2 indicated incomplete reaction. The toluene was distilled off, 25 mL of aniline was added and the mixture refluxed for 4 hours. Fifty mL of xylene was added and the reaction refluxed again for 3 hours. The solvent and excess aniline were removed in vacuo and the residue recrystallized from benzene to yield 19.9 g of crude product. This was recrystallized from approximately 1.5 L hexane to yield 15.8 g (86%) of product, m.p. 125°–126° C.

EXAMPLE 2

N-[[1-[[2-(Diethylamino)ethyl]amino]-9-oxothioxanthen-4-yl]methyl]formamide (I: $R^1=R^2=Et$; $Q=CH_2NHCHO$; $R^8=H$; n=2)

A solution of 35.4 g (0.1 mmol) of 1-[[2-(diethylamino)ethyl]amino]-9-oxo-thioxanthen-4-carboxyaldehyde, 420 mL of formamide and 50 mL (1 mol) of formic acid was heated at 160° for 1 hour. The reaction was cooled, poured into 2 L of water and made basic with about 50 mL of 35% sodium hydroxide solution. The gummy precipitate was filtered off and dried in vacuo. The dried precipitate was dissolved in about 1.5 L of hot ethyl acetate, treated with charcoal, and crystallized by cooling. The product was filtered off, washed with ethyl acetate and dried to provide 29.0 g (75%) of product, m.p. 154°–155° C.

EXAMPLE 3

N-[[1-[[2-(Diethylamino)ethyl]amino]-9-oxothioxanthen-4-yl]methyl]-N-methylformamide (IV: $R^1=R^2=Et$; $R^4=Me$; $R^8=H$; n=2)

By a procedure analogous to that of Example 2, 24.6 g of the N-methylformamide was prepared from 35.4 g (0.1 mol) of 1-[[2-(diethylamino)ethyl]amino]-9-oxo-thioxanthen-4-carboxyaldehyde, 394 g of N-methylformamide and 50 mL of formic acid. The product was recrystallized from 150 mL of acetone to a m.p. of 127°–130° C.

EXAMPLE 4

4-(Aminomethyl)-1-[[2-(diethylamino)ethyl]amino]-thioxanthen-9-one (I: $R^1=R^2=Et$; $Q=CH_2NH_2$; $R^8=H$; n=2)

A solution of 24.4 g (64 mmol) of the formamide of Example 2 in 240 mL of 2N hydrochloric acid was heated on a steam bath for 1 hour. The reaction was cooled to room temperature, made basic with 35% aqueous sodium hydroxide, and the resulting yellow precipitate collected by filtration. The product was dissolved in benzene, treated with charcoal, dried with magnesium sulfate, filtered and azeotroped to remove traces of water. The dried residue was crystallized from methanol and isopropanol by the addition of ethereal hydrogen chloride. The resulting solid was recrystallized in several crops from methanol to yield 10.6 g of product, m.p. 270°–272°, as the dihydrochloride salt.

EXAMPLE 5

1-[[2-(Diethylamino)ethyl]amino]-4-[(methylamino)methyl]thioxanthen-9-one (I: $R^1=R^2=Et$; $Q=CH_2NHCH_3$; $R^8=H$; n=2)

By a process precisely analogous to that of Example 4, 10.5 g of the methylamine was obtained as the dihydrochloride hemihydrate from 14.6 g (37 mmol) of the N-methylformamide of Example 3 and 150 mL of 2N hydrochloric acid. The product melted at 241°–243°.

EXAMPLE 6

N-[[1-[[2-(Diethylamino)ethyl]amino]-9-oxothioxanthen-4-yl]methyl]methanesulfonamide (I: $R^1=R^2=Et$; $Q=CH_2NHSO_2CH_3$; $R^8=H$; n=2)

A solution of 10.65 g (30 mmol) of the free base of the amine of Example 4 in 100 mL of pyridine was cooled in an ice bath and 4 g (35 mmol) of methanesulfonylchloride was added in one portion. The mixture was stirred for 2 hours at room temperature and poured into 750 mL of water containing 2 g of sodium hydroxide. The dark yellow precipitate was collected, washed with water and dried in vacuo overnight. A second crop was obtained by adding excess sodium hydroxide to the filtrate and filtering the resulting solid. The combined precipitates after drying were recrystallized from benzene to yield 6.4 g of the methanesulfonamide, m.p. 169°–170°.

EXAMPLE 7

1-[[2'-(Diethylamino)ethyl]amino]-9-oxothioxanthene-4-carboxamide (I: $R^1=R^2=Et$; $Q=CONH_2$; $R^8=H$; n=2)

A suspension of 74 g (0.23 mol) of 1-[[2-(diethylamino)ethyl]amino]-9-oxo-thioxanthen-4-carboxaldehyde and 74 g (1.06 mol) of hydroxylamine hydrochloride in 400 mL of pyridine and 400 mL of ethanol was refluxed 0.5 hour and 70 mL of water was added to provide a homogeneous solution. The solution was heated for a further 2 hours and allowed to sit at room temperature 14 hours. The resulting crystalline oxime was filtered off to provide a quantitative yield, mp 215°–218°.

One hundred twenty-three grams of the oxime was heated briefly on a steambath in 180 mL of acetic anhydride to achieve solution. The solution was cooled, 100 mL of 1.8M HCl in ether was added and the resulting suspension was diluted with 500 mL of ether. The suspension was allowed to sit 14 hours at 0° and filtered. The residue (123 g, mp 109°–112°) was slurried in 250 mL of xylene and refluxed 20 min. The mixture was cooled and 71.3 g of the nitrile was filtered off, mp 265°.

Ten grams of the nitrile was stirred in 200 mL of conc. $H_2SO_4$ at room temperature for 3 days. The reaction was neutralized with conc. $NH_4OH$ and the residue filtered off. The residue was digested in warm EtOAc/EtOH, filtered and the product crystallized from the chilled solution, mp 241°–243°. It was dissolved in ethanol and one equivalent of HCl in ethanol was added. Six grams of the amide hydrochloride was obtained, mp 271°–272°.

EXAMPLE 8

N-[[1-[[2-(Diethylamino)ethyl)amino]-9-oxothioxanthen-4-yl]methyl]N-methylmethanesulfonamide (I: $R^1=R^2=Et$; $Q=CH_2N(CH_3)SO_2CH_3$; $R^8=H$; n=2)

A solution of 1.5 g (3.5 retool) of the methanesulfonamide of Example 6 in THF (60 mL) was cooled to 0° C. in an ice-bath and NaH 0.16 g (4.0 mmol) was added. The reaction mixture was warmed to room temperature, stirred for 10 minutes, then methyl iodide 0.25 mL (4.0 mmol) was added. The reaction mixture was stirred at room temperature for 24 hours and the solvent was removed in vacuo. The residue was purified by column chromatography on silica eluting with chloroform (100%) then 1% isopropylamine/chloroform to afford 1.15 g (74%) of the N-methylmethanesulfonamide as a yellow powder, m.p. 175°–177° C. The free base was also treated with methanesulfonic acid in methanol to afford the methanesulfonate salt, m.p. 194°–195.5° C. (labelled Example 8a hereinafter).

EXAMPLE 9

N-[[1-[[2-(Diethylamino)ethyl]amino]-9-oxothioxanthen-4-yl]methyl]phenylsulfonamide (I: $R^1=R^2=Et$; $Q=CH_2NHSO_2Ph$; $R^8=H$; n=2)

Following a procedure substantially similar to that described in Example 6, 2.4 g (57%) of the phenylsulfonamide was obtained as the methanesulfonic acid salt from 2.54 g (7.15 mmol) of the free base of the amine of Example 4, pyridine (50 mL) and benzenesulfonyl chloride (1.1 mL, 8.62 mmol), followed by treatment with methanesulfonic acid in methanol. The product was recrystallized from ethanol.

EXAMPLE 10

N-[[1-[[2-(Diethylamino)ethyl]amino]-9-oxo-thioxanthen-4-yl]methyl]acetamide (I: $R^1=R^2=Et$; $Q=CH_2NHC(O)CH_3$; $R^8S=H$; n=2)

Following a procedure substantially similar to that described in Example 6, 2.3 g (52%) of the acetamide was obtained as an orange solid from 4.15 g (11.7 mmol) of the free base of the amine of Example 4, pyridine (60 mL) and acetyl chloride (0.82 mL, 11.53 mmol). The product was recrystallized from acetone and melted at 182°–183° C.

EXAMPLE 11

N-[[1-[[2-(Diethylamino)ethyl]amino]-9-oxothioxanthen-4-yl]methyl]benzamide (I: $R^1=R^2=Et$; $Q=CH_2NHC(O)Ph$; $R^8=H$; n=2)

Following a procedure substantially similar to that described in Example 6, 1.02 g (68%) of the benzamide was obtained as a yellow powder from 1.17 g (3.29 mmol) of the free base of the amine of Example 4, pyridine (25 mL) and benzoyl chloride (0.42 mL, 3.62 mmol). The product was purified by column chromatography on silica eluting with chloroform (100%) to isopropylamine/chloroform, followed by recrystallization from ethyl acetate. The product melted at 161°–163° C.

EXAMPLE 12

N-[[1-[[2-(Diethylamino)ethyl]amino]-9-oxothioxanthen-4-yl]diethylphosphoramide (I: $R^1=R^2=Et$; $Q=CH_2NHP(O)(OEt)_2$; $R^8=H$; n=2)

A solution of 2.28 g (6.41 mmol) of the free base of the amine of Example 4, $CH_2Cl_2$ (50 mL), and triethylamine (2 mL) at 0° C. was treated with diethyl phosphorochloridate (1.0 mL, 6.9 mmol). The reaction mixture was stirred at 0° C. for 2 hours, then at room temperature for 1 hour. The solvent was removed in vacuo and the residue was purified by column chromatography on silica eluting with ethyl acetate (100%), then 5% methanol/ethyl acetate and finally methanol/isopropylamine/ethyl acetate (5/5/90) to afford 2.28 g (72%) of the diethyl phosphoramide as a yellow solid, m.p. 108°–110° C. when recrystallized from ethyl acetate.

EXAMPLE 13

N-[[1-[[2-(Diethylamino)ethyl]amino]-9-oxothioxanthen-4 -yl]methyl]-N-ethylformamide (IV: $R^1=R^2=Et$; $R^4=Et$; $R^8=H$; n=2)

A solution of 2.0 g (5.6 mmol) of 1-[[2-(diethylamino)ethyl]amino]-9-oxo-thioxanthen-4-carboxaldehyde, N-ethylformamide (24.0 mL) and formic acid (3.0 mL, 79.5 mmol) was heated at 170° C. for 4 hours. The reaction mixture was cooled, poured into water and made basic with 10% sodium hydroxide. A solid was obtained which was collected by filtration and washed with water. The solid residue was taken up in chloroform/water, and the organic layer was separated and dried over Na$_2$SO$_4$. The solvent was removed in vacuo and the residue was purified by radial chromatography eluting with isopropylamine/methanol/ethyl acetate (0.5/1/98.5) to afford 1.32 g (57%) of the N-ethylformamide as an orange solid, m.p. 75°–77° C.

EXAMPLE 14

1-[[2-(Diethylamino)ethyl]amino]-4-[(ethylamino)-methyl]thioxanthen-9-one (I: R$^1$=R$^2$=Et; Q=CH$_2$NHC$_2$H$_5$; R$^8$=H; n=2)

By a process substantially similar to that described in Example 4, 1.29 g (92%) of the ethylamine was obtained as the dihydrochloride from 1.3 g (3.2 mmol) of the N-ethylformamide of Example 13 and 10.8 mL of 2N hydrochloric acid. The product was recrystallized from ethanol/tetrahydrofuran and melted at 160° C. (dec.).

EXAMPLE 15

1-[[2-(Diethylamino)]ethyl]amino]-4-(dimethylaminomethylene-aminomethyl)thioxanthen-9-one trihydrochloride (I: R$^1$=R$^2$=Et; Q=CH$_2$N=CHN(Me)$_2$; R$^8$=H; n=2)

N-[[1-[[2-(Diethylamino)]ethyl]amino]-9-oxothioxanthen-4-yl]methyl]formamide (3 g) was diluted with 50 mL of 2N HCl and the solution was heated on a steam bath for 90 min. The mixture was cooled, basified to pH 10 with 35% sodium hydroxide solution, and extracted into chloroform. The organic layer was separated, filtered through K$_2$CO$_3$, and concentrated in vacuo and the resulting crude product was allowed to react with dimethylformamide dimethyl acetal overnight at 60° C. Excess DMF-dimethyl acetal was removed in vacuo and the desired title compound was purified by flash chromatography (silica gel; chloro-form/iPrNH$_2$/MeOH (98:1:1). This product was dissolved in 2.5M HCl/EtOH (100 mL), cooled in an ice-bath, filtered, and dried to afford 2.38 g of 1-[[2-(diethylamino)]ethyl]amino]-4-(dimethylaminomethyleneaminomethyl)-thioxanthen-9-one trihydrochloride as a orange solid, m.p. 258°–260° C.

EXAMPLE 16

N-[[1-[[2-(Diethylamino)ethyl]amino]-9-oxothioxanthen-4-yl]methyl]-trifluoroacetamide (I: R$^1$=R$^2$=Et; Q=CH$_2$NHC(O)CF$_3$; R$^8$=H; n=2)

A solution of 4-(aminomethyl)-1-[[2-(diethylamino)ethyl]amino]thioxanthen-9-one (2.91 g; 8.19 mmol) in 80 mL of methylene chloride at 0° C. was treated with trifluoroacetyl chloride (14.75 mL of 0.61M solution in toluene; 9.0 mmol) and the reaction mixture was stirred at 0° C. for 90 min. The mixture was concentrated in vacuo and the residue was purified by flash chromatography (silica gel; EtOAc (100%), then 2% isopropylamine/EtOAc) and then recrystallization from ethyl acetate to afford 2.52 g (68%) of the product as the free base, m.p. 189°–190° C. (Example 16). The free base was dissolved in methanol and treated with methanesulfonic acid (0.55 g, 5.72 mmol) to afford the methanesulfonate salt, m.p. 152°–154° C. after recrystallization from acetone (Example 16a).

EXAMPLE 17

(a)

A mixture of thiosolicyclic acid (50.14 g, 0.33 mol) and cupric acetate (5.0 g) in DMSO (500 mL) was brought to reflux and potassium carbonate (54.3 g) was added in portions. 3-Bromochlorobenzene (42 mL, 0.36 mol) was then added via syringe and the mixture was refluxed for 3 hours. The reaction mixture was poured into water, treated with charcoal and filtered through celite. The filtrate was acidified with concentrated HCl and the precipitate which formed was collected by filtration, washed with water and dried in vacuo at 60° C. to afford 75.01 g (86%) of 2-[(3-chlorophenyl)thio]-benzoic acid.

(b)

To a stirred solution of concentrated H$_2$SO$_4$ at 0° C. was added 2-[(3-chlorophenyl)thio]benzoic acid (75.00 g, 0.28 mol) in portions over 1 hour. The mixture was stirred for 2 hours, poured into concentrated NH$_4$OH (500 mL) in water (2.5 L) and the precipitate which formed was collected by filtration, washed with water and dried in vacuo at 60° C. to afford 65.9 g (95%) of a mixture of 1-chloro and 3-chlorothioxanthen-9-one.

(c)

A mixture of 1-chloro and 3-chlorothioxanthen-9-one (14.01 g, 56.8 mmol), pyridine (20 mL) and diethylaminopropylamine (5.13 g, 39.4 mmol) was refluxed until the reaction was complete. The heat was removed, the solvent was removed in vacuo and the residue was taken up in chloroform and purified by column chromatography on silica eluting with chloroform to remove the unreacted 3-chloroisomer and then 5% isopropylamine/chloroform to afford 5.10 g (54%) of 1-[[3-(diethylamino)propyl]amino]-thioxanthen-9-one as an orange gum.

(d)

A mixture of 1-[[3-(diethylamino)propyl]amino]thioxanthen-9-one (5.10 g, 15.0 mmol), formalin (160 mL) and 5N acetic acid (0.8 mL) was heated to 90° C. 16 hours, additional 5N acetic acid (0.20 mL) was added, followed by formalin (50 mL) and the mixture was heated at 90° C. for approximately 57 hours. The mixture was diluted with water, basified with 5N NaOH and extracted with chloroform. The organic layer was dried over Na$_2$SO$_4$ and passed through a silica column eluting with 2% methanol/chloroform and then isopropylamine/methanol/chloroform (2/2/96) to afford 3.82 g (69%) of 1-[[3-(diethylamino)propyl]amino]-4-(hydroxymethyl)-thioxanthen-9-one as an orange/brown gum.

(e)

1-[[3-(Diethylamino)propyl]amino]-9-oxothioxanthen-4-carboxaldehyde (II: R$^1$=R$^2$=Et; R$^8$=H; n=3)

A mixture of 1-[[3-(diethyiamino)propyl]amino]-4-(hydroxymethyl) thioxanthen-9-one (3.82 g), toluene (60 mL) and manganese oxide (7.5 g) was refluxed for 6.5 hours. The mixture was cooled to room temperature, filtered through celite, and the filtrate was concentrated in vacuo to afford 3.3 g (87%) of 1-[[3-(diethylamino) propyl]amino]-9-oxothioxanthen-4-carboxaldehyde as a brown oil.

(f)

1-[[3-(Diethylamino)propyl]amino]-4-(methylaminomethyl) thioxanthen-9-one dihydrochloride 3/2 hydrate (I: $R^1=R^2=Et$; $Q=CH_2NHMe$; $R^8=H$; $n=3$)

A solution of 1-[[3-(diethylamino)propyl]amino]-9-oxothioxanthen-4-carboxaldehyde (3.3 g, 8.96 mmol) and 3 g of formic acid in 50 mL of N-methylformamide was allowed to reflux for 2 h. The mixture was basified with 5 mL of a 5N sodium hydroxide solution and extracted into chloroform (3×150ml). The organic layer was dried over sodium sulfate, concentrated in vacuo, and a crude oil was dissolved in a 3N aqueous HCl solution (50 ml) and heated on a steam bath for 3 h. The above mixture was cooled, basified with 30 mL of 35% NaOH, extracted into chloroform (3×150ml), the organic layer dried over sodium sulfate and concentrated in vacuo to afford a brown oil. The brown oil was purified by flash chromatography (silica gel; 5% triethylamine/Et2O, then 5% Et3N/EtOAc, then triethylamine/methanol/EtOAc (5:5:90)) to afford 1.1 g of 1-[[3-(diethylamino)propyl]amino]-4-(methylaminomethyl)thioxanthen-9-one, as a clear orange gum. The above gum was converted into the corresponding dihydrochloride by treatment with 6N HCl in ether to afford 1.04 g of the dihydrochloride.3/2 hydrate as a yellow powder, m.p. 222°-224° C.

EXAMPLE 18

(a)

A mixture of 1-chloro and 3-chlorothioxanthen-9-one (20 g), pyridine (40 mL) and N,N-dimethylethylene diamine (11 mL) was refluxed for approximately 22 hours and then the solvent was removed in vacuo. The residue was combined with the crude product (3.51 g) obtained from three similar experimental runs and the mixture was purified by column chromatography on silica eluting with chloroform, then 1% isopropylamine/chloroform and finally 2% isopropylamine/chloroform to afford 13.4 g of 1-[[2-(dimethylamino) ethyl]amino]thioxanthen-9-one.

(b)

A mixture of 1-[[2-(dimethylamino)ethyl]amino]thioxanthen-9-one (13 g, 0.044 mol) , 37% formalin (390 mL) and 5N acetic acid (6.5 mL) was heated to 100° C. for 8.5 hours, allowed to stand over the weekend and then was heated at 100° C. for several more hours. The mixture was poured into ice water, basified with 35% NaOH and extracted with chloroform. The organic layer was washed with brine, dried over Na2SO4 and concentrated in vacuo. The residue was purified by column chromatography on silica eluting in succession with; 25% CHCL3/hexane; 50% CHCl3/hexane; 75% CHCl3/hexane; 100% CHCl3; 0.5% isopropylamine/chloroform; 1% isopropylamine/chloroform; 2% isopropylamine/chloroform; then 2% isopropylamine/2% MeOH/CHCl3 to afford 9.2 g (64%) of 1-[[2-(dimethylamino) ethyl]amino]-4-(hydroxymethyl)thioxanthen-9-one.

(c)

A mixture of 1-[[2-(dimethylamino)ethyl]amino]-4-(hydroxymethyl)thioxanthen-9-one (9.2 g, 0.028 mol) in toluene (322 mL) was heated to about 60° C. and then manganese oxide (MnO2, 16 g) was added and the mixture was heated at 60° C. for 1 hour. The mixture was filtered and the filtrate was concentrated in vacuo to afford 7.9 g (87%) of 1-[[2-(dimethylamino)ethyl]amino]-9-oxothioxanthen-4-carboxaldehyde (Formula II: $R^1=R^2=Me$; $R^8=H$; $n=2$).

(d)

N-[[1-[[2-(Dimethylamino)ethyl]amino]-9-oxothioxanthen-4-yl]methyl]formamide (I: $R^1=R^2=Me$; $Q=CH_2NHCHO$; $R^8=H$; $n=2$)

A mixture of 1-[[2-(dimethylamino)ethyl]amino]-9-oxothioxanthen-4-carboxaldehyde (4.75 g) , formamide (66.5 mL) and formic acid (7.6 mL) was heated at 170° C. for 4 hours. The mixture was poured into ice water (250 mL) , basified with 35% NaOH and extracted with chloroform. The organic layer was washed with water (2×), then brine (1×) and the solvent was dried over Na2SO4 and concentrated in vacuo to afford 6.2 g of N-[[1-[[2-(dimethylamino) ethyl]amino]-9-oxothioxanthen-4-yl ]methyl ]formamide.

(e)

4-(Aminomethyl)-1-[[2-(dimethylamino)ethyl]amino]-9-oxothioxanthen-9-one dihydrochloride.½hydrate (I: $R^1=R^2=Me$; $Q=CH_2NH_2$; $R^8=H$; $n=2$ )

A mixture of N-[[1-[[2-(dimethylamino)ethyl]amino]-9-oxothioxanthen-4-yl]methyl]formamide (6.2 g) and 2N HCl (52 mL) was heated to 100° C. for 1.5-2 hours. The reaction mixture was poured into ice water, basified with 35% NaOH, and extracted with chloroform. The organic layer was washed with water (2×), then brine (1×), dried over Na2SO4 and concentrated in vacuo. The residue was purified by column chromatography on silica eluting with ethyl acetate, then 0.5% triethylamine/EtOAc, then 2% triethylamine/EtOAc, then CHCl3/1-2% isopropylamine and finally CHCl3/1-2% isopropylamine/2% MeOH to afford 3.3 g (58%) of the product as the free base. A portion of the free base (1.25 g) was dissolved in methanol and treated with concentrated HCl (3.3 mL) in MeOH (6 mL) to afford 1.2 g of the product as the dihydrochloride.½hydrate, m.p. 213° C. (dec.).

(f)

N-[[1-[[2-(Dimethylamino)ethyl]amino]-9-oxothioxanthen-4-yl]methyl]methanesulfonamide methanesulfonate (I: $R^1=R^2=Me$; $Q=CH_2NHSO_2Me$; $R^8=H$; $n=2$)

4-(Aminomethyl)-1-[[2-(dimethylamino)]ethyl]amino]-thioxanthen-9-one (2 g, 6 mmol) in 30 mL of dry pyridine under nitrogen was stirred at room temperature until the solution was complete. The solution was chilled in an ice-bath and 0.52 mL (6.7 mmol) of methanesulfonyl chloride in chilled pyridine was added dropwise and the mixture was stirred for 1 h at room temperature. The reaction mixture was poured into 500 mL of water containing 0.51 g of sodium hydroxide, extracted into chloroform, the organic layer was washed with water (2×) and brine, and dried over anhydrous sodium sulfate. The mixture was filtered and concentrated in vacuo. The residue (2.5 g) was stirred in ether, filtered, and dried to afford 2 g of N-[[1-[[2-(dimethylamino) ethyl]amino]-9-oxothioxanthen-4-yl]methyl]methanesulfonamide, m.p. 126°-127° C. The free base was dissolved in MeOH, and treated with methanesulfonic acid (0.48 g) to afford 2.0 g (67%) of the product as the methanesulfonate salt, m.p. 168° C. (dec.).

EXAMPLE 19

(a)

Following a procedure similar to that described in Example 17(c), there was prepared 6.83 g of 1-[[3-(dimethylamino)propyl]amino]thioxanthen-9-one, from a mixture of 1-chloro and 3-chlorothioxanthen-9-one (15.15 g, 61.4 mmol), pyridine (20 mL) and dimethylaminopropylamine (6.01 g, 58.7 mmol).

(b)

Following a procedure similar to that described in Example 17(d), there was obtained 6.74 g (90%) of 1-[[3-(dimethylamino) propyl]amino]-4-(hydroxymethyl) thioxanthen-9-one, from 1-[[3-(dimethylamino)propyl]amino]thioxanthen-9-one (6.8 g, 21.8 mmol), formalin (175 mL) and glacial acetic acid (0.75 mL).

(c)

Following a procedure similar to that described in Example 17(e), there was obtained 4.2 g of 1-[[3-(dimethylamino)propyl]amino]-9-oxothioxanthen-4-carboxaldehyde (Formula II: $R^1=R^2=Me$; $R^8=H$; n=3) from 1-[[3-(dimethylamino)propyl]amino]-4-(hydroxymethyl) thioxanthen-9-one (6.7 g), toluene (80 mL) and MnO$_2$ (12.15 g). The product was purified by column chromatography on silica eluting with CHCl$_3$ (1.00%) to 1% isopropylamine/CHCl$_3$.

(d)

A mixture of N-methylformamide (50 mL), formic acid (5.2 g) and 1-[[3-(dimethylamine)propyl]amino]-9-oxothioxanthen-4-carboxaldehyde (4.14 g, 12.16 mmol) was refluxed for 3 hours. The mixture was diluted with water (250 mL), basified with 35% NaOH and extracted with CHCl$_3$ (3×150 mL). The organic layer was dried over Na$_2$SO$_4$, passed through a plug of silica eluting with CHCl$_3$ (100%), then 2% isopropylamine/CHCl$_3$ to afford 3.93 g (84%) of N-[[1-[[3-(dimethylamino)-propyl]amino]-9-oxothioxanthen-4-yl]methyl]-N-methylformamide (Formula IV: $R^1=R^2=Me$; $R^4=Me$; $R^8=H$; n=3).

(e)

1-[[3-(Dimethylamino)propyl]amino]-4-[(methylaminomethyl]thioxanthen-9-one dihydrochloride monohydrate ($R^1=R^2=Me$; Q=CH$_2$NHMe; $R^8=H$; n=3)

A solution of the above N-methylformamide (3.83 g; 10 mmol) in 40 mL of 3N HCl was heated on a steam bath for 4 h; neutralized with 35% NaOH solution, and chilled on ice for 1 h. The liquid layer was decanted and a crude product was dissolved in chloroform and filtered through silica gel (chloroform; 1% isopropylamine/chloroform) to afford 2.38 g of the desired amine as an orange gum. The product was converted into the corresponding hydrochloride salt by dissolution in MeOH and treatment with concentrated HCl to afford 0.98 g of the dihydrochloride monohydrate, m.p. 228°–229° C.

EXAMPLE 20

(a)

A mixture of 1-[[2-(dimethylamino)ethyl]amino]-9-oxothio-xanthen-4-carboxaldehyde (4.75 g, 0.15 mol), N-methylformamide (48 mL) and formic acid (3.9 mL) was heated at 170° C. for 4.5 hours and then was allowed to stand at room temperature for approximately 64 hours. The reaction mixture was poured into water (250 mL), basified with 35% NaOH, extracted with CHCl$_3$ (3×). The organic layer was separated, washed with water (2×) and then brine (1×) and was dried over Na$_2$SO$_4$. The solvent was removed in vacuo to afford 5.75 g of N-[[1-[[2-(dimethylamino) ethyl]amino]-9-oxothioxanthen-4-yl]methyl]-N-methyl formamide [Formula IV: $R^1=R^2=Me$; $R^4=Me$; $R^8=H$; n=2)

(b)

1-[[2-(Dimethylamino)ethyl]amino]-4-[(methylamino) methyl]thioxanthen-9-one dihydrochloride.5/4 hydrate (I: $R^1=R^2=Me$; Q=CH$_2$NHMe; $R^8=H$; n=2)

By a process similar to that of Example 19E, 1.8 g of 1-[[2-(dimethylamino) ethyl]amino]-4-[(methylamino)-methyl]thioxanthen-9-one was obtained from 5.7 g (15.4 mmol) of the corresponding N-methylformamide of Example 20(a) and 50 mL of 2N HCl, after purification of the free base by flash chromatography (silica gel; chloroform; then 0.5% isopropylamine/chloroform; then 1% isopropylamine/chloroform). The free base was converted into the corresponding dihydrochloride 5/4 hydrate salt by treating with conc. HCl in methanol to afford 1.8 g (30%) of the product, m.p. 177° C. (dec.).

EXAMPLE 21

(a)

A solution of 1-[[3-(dimethylamino) propyl]amino]-9-oxothio-xanthen-4-carboxaldehyde (3.6 g; 10.57 mmol) in 50 mL of formamide containing 3.6 g of formic acid was refluxed for 1.5 h and then was allowed to stand at room temperature overnight. The reaction mixture was diluted with water (400 ml), basified with 3 mL of 5N NaOH solution, stirred rapidly for 30 min, and the precipitated solid was filtered, washed with water, and dried, yielding 3.1 g (79%) of N-[[1-[[3-(dimethylamino)propyl]amino]-9-oxothioxanthen-4-yl]methyl]formamide (Formula I: $R^1=R^2=Me$; Q=CH$_2$NHCHO; $R^8=H$; n=3), as a yellow powder.

(b)

A solution of the formamide of Example 21(a) (2.98 g; 8.07 mmol) in 40 mL of 3N HCl was heated on a steam bath for 4 h, allowed to cool to room temperature, chilled in ice, and neutralized to pH 8 with 5N NaOH solution. The resulting heterogenous mixture was extracted into chloroform (5×100 ml) and the organic layer was dried over sodium sulfate and filtered through a pad of silica gel (first 5% triethylamine/ether, then 1–5% isopropylamine/chloroform) to afford 2.3 g (83%) of 4-(aminomethyl)-1-[[3-(dimethylamino) propyl]amino]thioxanthen-9-one (Formula I: $R^1=R^2=Me$; Q=CH$_2$NH$_2$; $R^8=H$; n=3), as a bright yellow oil.

(c)

N-[[1-[[3-(Dimethylamino)propyl]amino]-9-oxothioxanthen-4-yl]methyl]methanesulfonamide methanesulfonate.½hydrate (I: $R^1=R^2=$Me; Q=CH$_2$NHSO$_2$Me; $R^8=$H; n=3)

To an ice cold solution of the amine of Example 21(b) (2.2 g; 6.44 mmol) in pyridine was added methanesulfonyl chloride (0.51 ml; 6.59 mmol) and the resulting mixture was stirred at room temperature overnight. The mixture was diluted with chloroform and passed through a large plug of silica gel eluting with 5% triethylamine/EtOAc affording 1.32 g of N-[[1-[[3-(dimethylamino) propyl]amino]-9-oxothioxanthen-4-yl]methyl]methanesulfonamide as a yellow powder. The free base was dissolved in methanol (10 mL) and treated with methanesulfonic acid (0.31 g, 1 eq.) in methanol to afford 1.38 g of the methanesulfonate.½hydrate salt as an orange solid, m.p. >107° C.

EXAMPLE 22

N-[[1-[[2-(Diethylamino)ethyl]amino]-9-oxothioxanthen-4-yl]methyl]-N-methyl-ethanesulfonamide methanesulfonate (I: $R^1=R^2=$Et; Q=CH$_2$N(CH$_3$)SO$_2$Et; $R^8=$H; n=2)

A solution of 2.03 g (5.49 mmol) of 1-[[2-(diethylamino)ethyl]amino]-4-[(methylamino)methyl]thioxanthen-9-one (prepared by the method described in Example 5) and triethylamine in 45 mL of methylene chloride was cooled to 0° C. and treated with ethanesulfonyl chloride (0.74 g, 5.76 mmol). After 15 min at 0° C., the reaction mixture was stirred at room temperature for 72 h. The mixture was concentrated in vacuo, the residue dissolved in chloroform and purified by passing through a pad of silica gel (chloroform; then 1% triethylamine/chloroform) affording 2.43 g (96%) of N-[[1-[[2-(diethylamino)ethyl]amino]-9-oxothioxanthen-4-yl]methyl]-N-methylethanesulfonamide. The sulfonamide was recrystallized from ethyl acetate and treated with methanesulfonic acid in isopropanol to afford the product as the methanesulfonate salt, m.p. 159°–161° C.

EXAMPLE 23

N-[[1-[[2-(Diethylamino)ethyl]amino]-9-oxothioxanthen-4-yl]methyl](p-methoxy)benzenesulfonamide methanesulfonate (I: $R^1=R^2=$Et; Q=CH$_2$NHSO$_2$C$_6$H$_4$-p-OMe; $R^8=$H; n=2)

A solution of 1.40 g (3.94 mmol) of 4-(aminomethyl)-1-[[2-(diethylamino) ethyl]amino]-thioxanthen-9-one (prepared by the method described in Example 4) in 30 mL of chloroform containing 1.5 mL of triethylamine was cooled to 0° C. and treated with p-methoxybenzenesulfonyl chloride (0.83 g, 4.02 mmol). After 10 min at 0° C. the reaction mixture was stirred at room temperature for 2 h. Chloroform was removed in vacuo, the residue dissolved in 100 mL of methylene chloride containing 1 mL of triethylamine and treated with additional p-methoxybenzenesulfonyl chloride (0.85 g) with stirring at room temperature. The mixture was concentrated in vacuo, the residue was purified by passing through a pad of silica gel (1% triethylamine/chloroform) affording 1.57 g of N-[[1-[[2-(diethylamino)ethyl]amino]-9-oxothioxanthen-4-yl]methyl]-p-methoxy-benzenesulfonamide. The sulfonamide was treated with methanesulfonic acid (0.3 g) in isopropanol/isopropyl acetate/methanol to afford 1.07 g of the methanesulfonate salt, m.p. 133°–137° C.

EXAMPLE 24

N-[[1-[[2-(Diethylamino)ethyl]amino]-9-oxothioxanthen-4-yl]methyl]ethanesulfonamide methanesulfonate (I: $R^1=R^2=$Et; Q=CH$_2$NHSO$_2$Et; $R^8=$H; n=2 )

A solution of 2.5 g of 4-(aminomethyl)-1-[[2-(diethylamino) ethyl]amino]-thioxanthen-9-one (prepared by the method described in Example 4) in 30 mL of pyridine was cooled in an ice bath for 15 min and 0.95 g of ethanesulfonyl chloride in 5 mL of pyridine was added rapidly dropwise and the reaction mixture was stirred at room temperature for 1 h. The mixture was poured into 75 mL of water containing 0.75 g of NaOH, extracted into chloroform, the organic layer was washed with water (2×) and brine, and dried over sodium sulfate. The mixture was concentrated in vacuo and the residue was stirred in ether and dried (40° C./0.1 mm) to afford 1.7 g of N-[[1-[[2-(diethylamino)ethyl]amino]-9-oxothioxanthen-4-Yl]methyl]ethanesulfonamide, m.p. 105° C. (dec.). The sulfonamide was dissolved in methanol and treated with methanesulfonic acid in methanol to afford 1.61 g (42%) of the methanesulfonate salt, m.p. 135° C. (dec.).

EXAMPLE 25

N-[[1-[[2-(Diethylamino)ethyl]amino]-9-oxothioxanthen-4-yl]methyl]-N-ethyl-methanesulfonamide (I: $R^1=R^2=$Et; Q=CH$_2$N(Et)SO$_2$Me; $R^8=$H; n=2 )

A solution of 2.10 g (5.48 mmol) of 1-[[2-(diethylamino) ethyl]amino]-4-[(ethylamino)methyl]thioxanthen-9-one (prepared by the method of Example 14) in 30 mL of methylene chloride was cooled to 0° C. and treated with 2 mL of triethylamine and methanesulfonyl chloride (0.7 ml) and the reaction mixture was stirred at room temperature for 6 h. The solvent was removed in vacuo, the residue dissolved in chloroform, and the solution was purified by passing through a pad of silica gel (eluting with chloroform followed by 2% triethylamine/chloroform). The yellow solid isolated was recrystallized from ethyl acetate and dried to afford 1.11 g (44%) of N-[[1-[[2-(diethylamino)ethyl]amino]-9-oxothixanthen-4-yl]methyl]-N-ethylmethanesulfonamide as a yellow powder, m.p. 172°–176° C.

EXAMPLE 26

N-[[1-[[2-(Diethylamino)ethyl]amino]-9-oxothioxanthen-4-yl]methyl]-3,4-dichlorobenzenesulfonamide methanesulfonate.½hydrate (I: $R^1=R^2=$Et; Q=CH$_2$NHSO$_2$C$_6$H$_3$-3,4-dichloro; $R^8=$H; n=2)

To a solution of 3,4-dichlorobenzenesulfonyl chloride (1.84 g, 7.5 mmol) in 35 mL of dry pyridine was added 2.5 g (7 mmol) of 4-(aminomethyl)-1-[[2-(diethylamino)ethyl]amino]-thioxanthen-9-one (prepared by the method described in Example 4) under nitrogen and the reaction mixture was stirred at room temperature for 15 min. and then was allowed to stand for approximately 72 hours. The reaction mixture was poured into 75 mL of water containing 0.75 g of NaOH, and extracted into chloroform. The organic layer was washed with water (2×) and brine, and dried over sodium sulfate. Chloroform was removed in vacuo, the residue was recrystallized from ethanol to afford 1.24 g of N-[[1-[[2-(diethylamino) ]ethyl]amino]-9-oxothioxanthen-4-yl]methyl]-3,4-dichlorobenzenesulfonamide, m.p. 95° C. (dec.). The free base was dissolved in methanol and treated with methanesulfonic acid in methanol to afford the methanesulfonate.½hydrate, m.p. 55° C. (dec.).

EXAMPLE 27

N-[[1-[[2-(Diethylamino)ethyl]amino]-9-oxothioxanthen-4-yl]methyl]-2-fluorobenzenesulfonamide (I: $R^1=R^2=Et$; $Q=CH_2NHSO_2C_6H_4$-2-F; $R^8=H$; n=2)

A solution of 1.36 g (3.83 mmol) of 4-(aminomethyl)-1-[[2-(diethylamino)ethyl]amino]-thioxanthen-9-one (prepared by the method described in Example 4) in 25 mL of methylene chloride containing 1 mL of triethylamine was cooled to 0° C. and treated with 2-fluorobenzenesulfonyl chloride (0.84 g; 4.32 mmol) and the reaction mixture was stirred for several hours. The solvent was removed in vacuo, the residue dissolved in chloroform, and purified by flash chromatography (silica gel: chloroform followed by 1% triethylamine/chloroform). The solvent was removed in vacuo and the product was recrystallized from ethyl acetate affording 1.08 g (55%) of N-[[1-[[2-(diethylamino)ethyl]amino]-9-oxothio-xanthen-4-yl]methyl]-2-fluorobenzenesulfonamide as an orange powder, m.p. 125°–127° C.

EXAMPLE 28

N-[[1-[[2-(Diethylamino)ethyl]amino]-9-oxothioxanthen-4-yl]methyl]-N-propyl-methanesulfonamide (I: $R^1=R^2=Et$; $Q=CH_2N(C_3H_7)SO_2Me$; $R^8=H$; n=2)

The oil from 0.2 g of 60% dispersion of sodium hydride in mineral oil was removed by triturating with pentane (4×). Dry DMF (40 ml) was added under nitrogen to sodium hydride with stirring, and 2 g of N-[[1-[[2-(diethylamino)ethyl]amino]-9-oxothioxanthen-4-yl]methyl]methanesulfonamide (Example 6) was then added to the reaction mixture while stirring under nitrogen and the mixture was heated to 50° C. for 2 h. The above mixture was chilled in an ice bath for 15 min, 0.87 g of propyl iodide in a small volume of DMF was added, and the mixture was allowed to stir at room temperature overnight. The mixture was stirred with 35 mL of water, filtered, and the residue was washed with water and dried (50° C./0.1 mm/$P_2O_5$) to afford 2.17 g of N-[[1-[[2-(diethylamino) ethyl]amino]-9-oxothioxanthen-4-yl]methyl]-N-propylmethanesulfonamide, m.p. 142°–143° C.

EXAMPLE 29

N-[[1-[[2-(Diethylamino)ethyl]amino]-9-oxothioxanthen-4-yl]methyl]-N-methyl-benzenesulfonamide methanesulfonate (I: $R^1=R^2=Et$; $Q=CH_2N(Me)SO_2C_6H_5$; $R^8=H$; n=2)

A solution of 5.32 g (14.4 mmol) of 1-[[2-(diethylamino) ethyl]amino]-4-[(methylamino]methyl]thioxanthen-9-one (prepared by the method described in Example 5) in 100 mL of methylene chloride was cooled to 0° C. and treated with triethylamine (5 ml) and benzenesulfonyl chloride (2 mL; 15.67 mmol) and the reaction mixture was stirred for 2 h. The mixture was concentrated in vacuo, and the residue was purified by passing through a pad of silica gel (eluting with chloroform; then ½%–1% isopropylamine/chloroform) yielding 6.24 g of a yellow gum. The product was dissolved in ethyl acetate and the solvent removed in vacuo affording 6.06 g (83%) of N-[[1-[[2-(diethylamino) ethyl]amino]-9-oxothioxanthen-4-yl]methyl]-N-methylbenzenesulfonamide. The sulfonamide (2.5 g) was suspended in isopropanol and treated with methanesulfonic acid (0.51 g) to yield 2.63 g of the methanesulfonate salt, m.p. 171°–174° C.

EXAMPLE 30

(a)

To a mixture of m-anisic acid (250 g, 1.67 mol) in acetic acid (1 L) was added bromine (85 mL) and then water (1 L). The mixture was heated to reflux, cooled in an ice bath and the product which precipitated was collected by filtration and washed with water to afford 305.7 g (79%) of 2-bromo-5-methoxybenzoic acid, m.p. 154°–156° C.

(b)

To a mixture of 3-chlorothiophenol (20 g, 0.138 mol), and cupric acetate (1.8 g) and DMF (200 mL) was added $K_2CO_3$ (23 g). The mixture was heated to 150° C. for 15–20 minutes, then 2-bromo-5-methoxybenzoic acid (35.8 g, 0.155 mol) was added in portions. The mixture was heated overnight, poured into water (600 mL), filtered and the filtrate was treated with charcoal, filtered and diluted with HCl. The resulting precipitate was collected by filtration, washed with water, and dried at 50° C. in vacuo over $P_2O_5$ to afford 27.6 g of 2-[(3-chlorophenyl) thio]-5-methoxybenzoic acid.

(c)

To cooled sulfuric acid (89 mL) under nitrogen was added 2-[(3-chlorophenyl)thio]-5-methoxybenzoic acid (27 g, 0.092 mol) in portions over 1.5–2 hours. The mixture was stirred at ambient temperature overnight, poured into water (900 mL) containing conc. NH$_4$OH (218 mL) and ice. The solid which precipitated was collected by filtration and dried at 50° C. in vacuo over $P_2O_5$ to afford 21 g (42%) of a mixture of 1-chloro and 3-chloro-7-methoxy-thioxanthen-9-one.

(d)

A mixture of 1-chloro and 3-chloro-7-methoxy-thioxanthen-9one (20.7 g), pyridine (69 mL) and diethylaminoethylamine (16.1 g, 0.138 mol) was heated at 115° C. under $N_2$ for 20 hours. The solvent was removed in vacuo and the residue was purified by column chromatography on silica eluting with $CHCl_3$ (100%) and then 1% isopropylamine/chloroform to afford 11.22 g of 1-[[2-(diethylamino) ethyl]amino]-7-methoxy-thioxanthen-9-one.

(e)

A mixture of 1-[[2-(diethylamino)ethyl]amino]-7-methoxy-thioxanthen-9-one (11.2 g, 0.031 mol), 37% formaldehyde (277 mL) and 5N acetic acid (4.6 mL) was heated at 100° C. for 3 hours. The reaction mixture was cooled, filtered, and the filtrate was poured into ice-water (600 mL) and made basic with 35% NaOH. The mixture was extracted with chloroform (3×), washed with brine and dried over $Na_2SO_4$. The solvent was removed in vacuo and the residue was purified by column chromatography on silica eluting with 25% CHCl₃/hexane, then 50% CHCl₃/hexane, then 75% CHCl₃/hexane, then 0.5% isopropylamine/CHCl₃ to afford 8.8 g (73%) of 1-[[2-(diethylamino)ethyl]amino]-4-(hydroxymethyl)-7-methoxythioxanthen-9-one.

(f)

A solution of 1-[[2-(diethylamino)ethyl]amino]-4-(hydroxymethyl)-7-methoxythioxanthen-9-one (8.8 g, 0.023 mol) in toluene (268 mL) was heated to 60° C. under nitrogen and then MnO₂ (13.2 g) was added. The mixture was heated overnight, filtered, and the filtrate was concentrated in vacuo to afford 7.05 g (81%) of 1-[[2-(diethylamino)ethyl]amino]-7-methoxy-9-oxothioxanthen-4-carboxaldehyde (Formula II: $R^1=R^2=Et$; $R^8=7\text{-OCH}_3$; n=2).

(g)

A solution of 1-[[2-(diethylamino)ethyl]amino]-7-methoxy-9-oxothioxanthen-4-carboxaldehyde (3 g, 7.8 mmol) and 1.5 mL of formic acid in 25.5 mL of N-methylformamide was heated to 170° C. for 8 h with stirring under nitrogen. The reaction mixture was poured into 160 mL of ice/water, basified with 35% of NaOH solution, and extracted into chloroform (3×). The organic layer was washed with water (2×) and brine, dried over sodium sulfate, and the solvent was removed in vacuo affording 3 g (89.9 %) of the desired N-[[1-[[2-(diethylamino)ethyl]amino]-7-methoxy-9-oxo-thioxanthen-4-yl]methyl]-N-methylformamide (Formula IV: $R^1=R^2=Et$; $R^4=Me$; $R^8=7\text{-OCH}_3$; n=2).

(h)

1-[[2-(Diethylamino)ethyl]amino]-4-[(methylamino)methyl]-7-methoxy-thioxanthen-9-one (I: $R^1=R^2=Et$; $Q=CH_2NHMe$; $R^8=7\text{-OMe}$; n=2)

The N-methylformamide of Example 30 (g) (3.0 g) in a 2N aqueous HCl solution (24 ml) was heated at 100° C. for 2 h under nitrogen with stirring. The above mixture was cooled, poured into 125 mL of ice/water, basified with 35% NaOH solution, and was extracted into chloroform and washed with water (2×), then brine. The organic layer was dried over sodium sulfate and concentrated in vacuo to afford 3.1 g of the crude product. The product was triturated in ether and the filtrate was purified by several flash chromatography columns (silica gel; eluting with 50% hexane/chloroform, then chloroform, and then 0.25–0.5% isopropylamine/chloroform (column 1); chloroform, then 1% isopropylamine/1% meOH/CHCl₃ (column 2); and CHCl₃, then 0.5% isopropylamine/CHCl₃ (column 3)) affording 0.746 g of 1-[[2-(diethylamino) ethyl]amino]-4-[(methylamino)methyl]-7-methoxy-thioxanthen-9-one.

EXAMPLE 31

(a)

N-[[1-[[2-(Diethylamino)ethyl]amino]-7-methoxy-9-oxothioxanthen-4-yl]methyl]formamide (I: $R^1=R^2=Et$; $Q=CH_2NHCHO$; $R^8=7\text{-OCH}_3$; n=2)

A mixture of 1-[[2-(diethylamino)ethyl]amino]-7-methoxy-9-oxothioxanthen-4-carboxaldehyde (3.6 g, 0.0094 mol), formamide (48 mL) nd formic acid (6 mL) was heated to 170° C. under N₂ for 8 hours. The mixture was poured into ice-water, basified with 35% NaOH and extracted with chloroform. The organic layer was separated, washed with water (2×), then brine and was dried over Na₂SO₄ and concentrated in vacuo to afford 3.88 g of N-[[1-[[2-(diethylamino) ethyl]amino]-7-methoxy-9-oxothioxanthen-4-yl]-methyl]formamide.

(b)

4-(Aminomethyl)-1-[[2-(diethylamino)ethyl]amino]-7-methoxy-thioxanthen-9-one (I: $R^1=R^2=Et$; $Q=CH_2NH_2$; $R^8=7\text{-OCH}_3$; n=2)

A mixture of the formamide of Example 31(a) (3.88 g) and 2N HCl (32 mL) was heated at 100° C. for 2 h under nitrogen with stirring. The above mixture was cooled, poured into water, basified with 10% NaOH solution, and extracted into chloroform and washed with water, then brine. The organic layer dried over sodium sulfate and concentrated in vacuo to afford 3.6 g of the crude product. The product was dissolved in chloroform and purified by flash chromatography (silica gel; eluting with hexane/chloroform (50:50) and then 1% isopropylamine in hexane/chloroform (50:50)) affording 1.75 g of the desired product.

(c)

N-[[1-[[2-(Diethylamino)]ethyl]amino]-7-methoxy-9-oxothioxanthen-4-yl]methyl]-methanesulfonamide (I: $R^1=R^2=Et$; $Q=CH_2NHSO_2Me$; $R^8=7\text{-OMe}$; n=2)

To a solution of 1.75 g (0.0045 mol) of the amine of Example 31(b) in 22.5 mL of pyridine cooled in an ice bath under nitrogen with stirring was added dropwise 0.39 mL (0.005 mol) of methanesulfonyl chloride in a small volume of pyridine and the resulting reaction mixture was stirred at room temperature for 2 h. The mixture was poured into 375 mL of water containing 0.38 g of NaOH, extracted into chloroform, and the organic layer was washed with water and brine. The chloroform layer was dried over sodium sulfate, the solvent removed in vacuo, and the residue was dried in vacuo to afford 1.61 g (77%) of N-[[1-[[2-(diethylamino) ethyl]amino]-7-methoxy-9-oxothioxanthen-4-yl]-methyl]methanesulfonamide, m.p. 144° C. (dec.).

EXAMPLE 32

(a)

To a mixture of 3-chlorothiophenol (20 g, 0.138 mol), cupric acetate (1.75 g) and DMF (199 mL) under N₂ was added in portions K₂CO₃ (23 g). The mixture was heated to 150° C. and then 2,5-dibromobenzoic acid (43.5 g) was added. The mixture was heated overnight, poured into water (600 mL), filtered, the filtrate was treated with charcoal and filtered again. The filtrate was acidified with conc. HCl, extracted with CHCl₃, the organic layer was washed with brine and dried over Na₂SO₄. The solvent was removed in vacuo to afford 28.9 g of 2-[(3-chlorophenyl)thio]-5-bromobenzoic acid.

(b)

A mixture of 2-[(3-chlorophenyl)thio]-5-bromobenzoic acid (28.4 g) and conc. sulfuric acid (80 mL) was stirred at 0° C. and then at room temperature overnight. The mixture was poured into ice-water (850 mL) containing conc. NH₄OH (199 mL) and the product which precipitated was collected by filtration and dried at 50° C. in vacuo to afford 15.0 g of a mixture of 1-chloro and 3-chloro-7-bromo-thioxanthen-9-one.

(c)

A mixture of 1-chloro and 3-chloro-7-bromothioxanthen-9-one (13.6 g), pyridine (108 mL) and N,N-diethylethylene diamine (16.3 mL) was heated to 115° C. for 20 hours. The solvent was removed in vacuo, and the residue was purified by column chromatography on silica eluting with CHCl$_3$ (100%), then 1% isopropylamine/CHCl$_3$ to afford 9.3 g of 1-[[2-(diethylamino)ethyl]amino]-7-bromothioxanthen-9-one.

(d)

A mixture of 1-[[2-(diethylamino)ethyl]amino]-7-bromothioxanthen-9-one (9.3 g, 22.9 mmol), 203 mL of 37% formaldehyde solution, and 3.4 mL of 5N acetic acid solution was heated to 100° C. under nitrogen overnight. The mixture was cooled to room temperature and the solid formed was removed by filtration. The filtrate was diluted with water, basified with 35% NaOH solution and extracted into chloroform. The organic layer was washed with brine, dried over sodium sulfate, and the solvent was removed in vacuo to afford 10 g of oil. The above oil in methylene chloride was filtered, the solvent concentrated in vacuo, and the crude hydroxymethyl analog was purified by flash chromatography (silica gel; eluting with 25% chloroform/hexane, then chloroform/hexane (1:1), then 25% chloroform/hexane, then CHCl$_3$ (100%), and then 0.5-1% isopropylamine/chloroform) to afford 3.2 g of 1-[[2-(diethylamino)ethyl]amino]-4-(hydroxymethyl)-7-bromothioxanthen-one.

(e)

1-[[2-(Diethylamino)ethyl]amino]-7-bromo-9-oxothioxanthen-4-carboxaldehyde (II: $R^1=R^2=Et$; $R^8=7-Br$; $n=2$)

A mixture of 3.2 g (7.34 mmol) of the alcohol of Example 32(d) and 4.3 g of MnO$_2$ in 85 mL of toluene was heated at 60° C. for 1 h under nitrogen. The mixture was filtered, washed with CHCl$_3$, and the combined filtrate was concentrated in vacuo affording 3 g of a yellow solid. The yellow solid was triturated in ether, filtered, and dried to afford 2.7 g (94.3%) of 1-[[2-(diethylamino)ethyl]amino]-7-bromo-9-oxothioxanthen-4-carboxaldehyde, m.p. 145°-146° C.

(f)

N-[[1-[[2-(Diethylamino)ethyl]amino]-7-bromo-9-oxothioxanthen-4-yl]methyl]formamide (I: $R^1=R^2=Et$; $Q=CH_2NHCHO$; $R^8=7-Br$; $n=2$)

A mixture of 2.7 g (6.2 mmol) of 1-[[2-(diethylamino)ethyl]amino]-7-bromo-9-oxothioxanthen-4-carboxaldehyde, 31.7 mL of formamide, and 3.6 mL of formic acid was heated to 170° C. under nitrogen and with stirring for 8 h and the mixture was allowed to stand at room temperature for 72 h. The mixture was poured into 150 mL of ice/water, basified with 35% NaOH solution, and the solid product was filtered and washed with water. The solid product was dissolved in chloroform, washed with brine, dried over sodium sulfate, and the solvent was concentrated in vacuo to afford 2.85 g of the desired formamide, as a yellow/orange solid, m.p. 132° C. (dec.).

(g)

1-[[2-(Diethylamino)ethyl]amino]-4-(aminomethyl)-7-bromothioxanthen-9-one (I: $R^1=R^2=Et$; $Q=CH_2NH_2$; $R^8=7-Br$; $n=2$)

A mixture of 2.85 g (6.6 mmol) of the above formamide (Example 32(f)) in 26 mL of 2N HCl solution was heated to 100° C. under nitrogen for 2 h and the mixture was allowed to stand at room temperature overnight. The reaction mixture was poured into 200 mL of ice/water, basified with 35% NaOH solution, and extracted into chloroform. The organic layer was washed with water and brine, dried over sodium sulfate, and concentrated in vacuo to yield 2.67 g of a dark oil. The dark oil was purified by flash chromatography (silica gel; 1250 mL of hexane/chloroform (1:1), and then 1% isopropylamine in hexane/chloroform (1:1)) to afford 1.87 g (70%) of 1-[[2-(diethylamino)ethyl]amino]-4-(aminomethyl)-7-bromothioxanthen-9-one, m.p. 79°-82° C.

EXAMPLE 33

N-[[1-[[2-(Diethylamino)ethyl]amino]-7-bromo-9-oxothioxanthen-4-yl]methyl]methanesulfonamide (I: $R^1=R^2=Et$; $Q=CH_2NHSO_2Me$; $R^8=7-Br$; $n=2$)

1-[[2-(Diethylamino)ethyl]amino]-4-(aminomethyl)-7-bromothioxanthen-9-one (1 g, 2.3 mmol) in 11.5 mL of dry pyridine under nitrogen was stirred in an ice bath for 15 min and 0.2 mL (2.6 mmol) of methanesulfonyl chloride in chilled pyridine was added dropwise and the mixture was stirred at room temperature. The reaction mixture was poured into 200 mL of water, added 0.19 g of sodium hydroxide in ice/water, and extracted into chloroform. The organic layer was washed with water (2×) and brine, and dried over anhydrous sodium sulfate. The mixture was filtered, concentrated in vacuo and the residue was stirred in ether, filtered, and dried to afford 1.02 g of N-[[1-[[2-(diethylamino) ethyl]amino]-7-bromo-9-oxothioxanthen-4-yl]methyl]methanesulfonamide, m.p. 134°-139° C.

EXAMPLE 34

Methyl N-[[1-[[2-(diethylamino)ethyl]amino]-9-oxothioxanthen-4-yl]methyl]carbamate (I: $R^1=R^2=Et$; $Q=CH_2NHCOOMe$; $R^8=H$; $n=2$)

To a solution of 2.94 g (8.27 mmol) of 4-(aminomethyl) -1-[[2-(diethylamino)]ethyl]amino]-thioxanthen-9-one in 50 mL of methylene chloride containing 5 mL of triethylamine chilled to 0° C. was added 0.7 mL (9.06 mmol) of methyl chloroformate and the mixture was stirred for 2.5 h. The solvent was removed in vacuo, the residue was suspended in chloroform and was purified by flash chromatography (silica gel; chloroform, then 1% isopropylamine/chloroform) affording 2.36 g (69%) of methyl N-[[1-[[2-(diethylamino)ethyl]amino]-9-oxothioxanthen-4-yl]methyl]carbamate, as a yellow solid, m.p. 129°-131° C.

EXAMPLE 35

1-[[2-(Diethylamino)ethyl]amino]-4-[(methylamino)methyl]-7-hydroxy-thioxanthen-9-one (I: $R^1=R^2=Et$; $Q=CH_2NHMe$; $R^8=7$-OH; n=2)

A solution of 1.6 g (4 mmol) of 1-[[2-(diethylamino)ethyl]amino]-4 -[(methyl-amino]methyl]-7 -methoxy-thioxanthen-9-one (prepared by the process described in Example 30(h)) in 10 mL of a 48% HBr solution was heated to 110° C. for 5 h. After cooling, the reaction mixture was neutralized with saturated sodium bicarbonate and extracted into chloroform (3×100ml). A dark gum, insoluble in water or chloroform, was dissolved in methanol and combined with chloroform solution. The solvent was concentrated in vacuo to afford 1.67 g of a dark orange solid. The orange solid product was purified by flash chromatography (silica gel; isopropylamine/methanol/chloroform (1:1:98) followed by a second silica column eluting with iso-propylamine/MeOH/CHCl₃ (2:2:96)) affording 0.56 g (36%) of 1-[[2-(diethylamino)ethyl]amino]-4-[(methylamino]methyl]-7-hydroxy-thioxanthen-9-one, m.p. 167°-169° C.

EXAMPLE 36

Methyl N-[[1-[[2-(diethylamino)]ethyl]amino]-7-methoxy-9-oxothioxanthen-4-yl]-methyl]carbamate (I: $R^1=R^2=Et$; $Q=CH_2NHCOOMe$; $R^8=7$-OMe; n=2)

To a solution of 1.55 g of 4-(aminomethyl) -1-[[2-(diethylamino)ethyl]amino]-7-methoxythioxanthen-9-one in 40 mL of chloroform containing 2 mL of triethylamine chilled to 0° C. was added 0.45 mL of methyl chloroformate and the mixture was stirred at room temperature for several hours. The solvent was removed in vacuo, the residue was purified by flash chromatography (silica gel; eluting with chloroform, then 1% triethylamine in chloroform/hexane (1:1)) affording 1.2 g of methyl N-[[1-[[2-(diethylamino) ethyl]amino]-7-methoxy-9-oxothioxanthen-4-yl]methyl]carbamate which was recrystallized from ethyl acetate to yield 0.79 g of a bright yellow solid, m.p. 131°-132° C.

EXAMPLE 37

N-[[1-(2-Diethylamino)ethyl]amino]-7-hydroxy-9-oxothioxanthen-4-yl]methyl]methanesulfonamide. ¾hydrate (I: $R^1=R^2=Et$, $Q=CH_2NHSO_2CH_3$; $R^8=7$-OH; n=2)

To a solution of N-[[1-(2-(diethylamino)ethyl]amino]-7-methoxy-9-oxothioxanthen-4-yl]methyl]methanesulfonamide (0.5 g) in CH₂Cl₂ (45 mL) at −78° C. was added 1N BBr₃ in CH₂Cl₂ (1.75 mL). The mixture was warmed to room temperature, stirred overnight, and then poured into ice-water (250 mL) containing 35% NaOH (8 mL). The mixture was acidified with dilute HCl, then basified with solid Na₂CO₃ and then was extracted with ethyl acetate. The organic layer was separated, washed with brine, dried over Na₂SO₄ and concentrated in vacuo. The residue was purified by column chromatography on silica eluting with 5% MeOH/EtOAc to afford 0.28 g (58%) of N-[[1-(2-diethylamino)ethyl]amino]-7-hydroxy-9-oxothioxanthen-4-yl]methanesulfonamide.¾hydrate, m.p. 78° C. (dec.).

EXAMPLE 38

4-(Aminomethyl)-1-[[2-(diethylamino)ethyl]amino]-6-methyl-thioxanthen-9-one (I: $R^1=R^2=Et$; $Q=CH_2NH_2$; $R^8=6$-CH₃; n=2)

Following a procedure similar to that described in Example 30, parts a-f, but substituting 4-methylbenzoic acid for 3-methoxybenzoic acid in part a, it is contemplated that there can be prepared 1-[[2-(diethy-2-amino)ethyl]amino]-6-methyl-9-oxothioxanthen-4-carboxaldehyde. It is further contemplated that the latter can be converted into 4-(aminomethyl)-1-[[2-(diethylamino)ethyl]amino]-6-methyl-thioxanthen-9-one by following procedures similar to those described in Example 31, parts a-b.

EXAMPLES 39–41

Following a procedure similar to that described in Example 34, but substituting, if necessary, an appropriate amine of the formula V for 4-(aminomethyl)-1-[[2-(diethylamino)ethyl]amino]-thioxanthen-9-one it is contemplated that the following compounds of formula I can be prepared:

[Structure of formula I with substituents $R^1$, $R^2$, $R^8$, Q, and NH(CH₂)ₙN group on thioxanthen-9-one]

| Example No. | $R^1$ | $R^2$ | n | Q | $R^8$ |
|---|---|---|---|---|---|
| 39 | C₂H₅ | C₂H₅ | 2 | CH₂NHC(O)OC₆H₅ | H |
| 40 | C₂H₅ | C₂H₅ | 2 | CH₂N(CH₃)C(O)O-4-CH₃—C₆H₄ | 7-OCH₃ |
| 41 | C₂H₅ | C₂H₅ | 2 | CH₂NHC(O)O-2-NO₂—C₆H₄ | 6-CH₃ |

EXAMPLE 42

1-[[2-Diethylamino)ethyl]amino]-4-[(methylamino)methyl]-6-methyl-thioxanthen-9-one (I: $R^1=R^2=Et$; $Q=CH_2NHCH_3$; $R^8=6$-CH₃; n=2)

Following a procedure similar to that described in Example 30, parts g-h. but substituting 1-[[2-(diethylamino)ethyl]amino]-6-methyl-9-oxo-thioxanthen-4-carboxaldehyde for 1-[[2-(diethylamino) ethyl]amino]-7-methoxy-9-oxo-thioxanthen-4-carboxaldehyde, there can be prepared 1-[[2-(diethylamino)ethyl]amino]-4(methylamino) methyl]-6-methyl-thioxanthen-9-one.

EXAMPLE 43

N-[[1-[[2-(Diethylamino)ethyl]amino]-6-methyl-9-oxothioxanthen-4-yl]methyl]methanesulfonamide (I: $R^1=R^2=Et$; $Q=CH_2NHSO_2CH_3$; $R^8=6$-CH₃; n=2)

Following a procedure similar to that described in Example 6, it is contemplated that N-[[1-[[2-(diethylamino)ethyl]amino]-6-methyl-9-oxothioxanthen-4-yl]methyl]methanesulfonamide can be prepared from 4-(aminomethyl) -1-[[2-(diethylamino)ethyl]amino]-6- methyl-thioxanthen-9-one, pyridine and methanesulfonyl chloride.

EXAMPLE 44

N-[[1-[[2-(Diethylamino)ethyl]amino]-7-methoxy-9-oxothioxanthen-4-yl]methyl]phenylsulfonamide (I: $R^1=R^2=Et$; $Q=CH_2NHSO_2Ph$; $R^8=7\text{-}CH_3O$; n=2)

Following a procedure similar to that described in Example 31, part c, it is contemplated that N-[[1-[[2-(diethylamino)ethyl]amino]-7-methoxy-9-oxothioxanthen-4-yl]methyl]phenylsulfonamide can be prepared from 4-(aminomethyl) -1-[[2-(diethylamino) ethyl]amino]-7-methoxy-thioxanthen-9-one, pyridine and benzenesulfonyl chloride.

EXAMPLE 45

(a)

N-[[1-[[2-(Diethylamino)ethyl]amino]-9-oxothioxanthen-4-yl]methyl]-N-phenylformamide (IV: $R^1=R^2=Et$; $R^4=Ph$; $R^8=H$; n=2)

A mixture of 1-[[2-(diethylamino)ethyl]amino]-9-oxothioxanthen-4-carboxaldehyde (3.40 g, 9.59 mmol), formanilide (31 g) and formic acid (3 mL) were heated to 160° C. for 2 hours. The mixture was cooled, poured into water (200 mL) and extracted with ether (3×150 mL). The aqueous layer was basified with 5N NaOH, extracted with CHCl₃ (3×150 mL) and the combined organic extracts were dried over Na₂SO₄ and filtered through florisil eluting with CHCl₃ (100%), then 5% isopropylamine / CHCl₃. The solvent was removed in vacuo and the residue was purified by column chromatography on silica eluting with 0.5% to 1% isopropylamine / CHCl₃ and then by recrystallization from benzene/hexane (2×) to afford 1.88 g of the desired product.

(b)

1-[[2-(Diethylamino)ethyl]amino]-4-[(phenylamino)methyl]thioxanthen-9-one (V: $R^1=R^2=Et$; $R^4=Ph$; $R^8=H$; n=2)

A mixture of the N-phenylformamide of Example 45(a) (1.70 g, 3.70 mmol) and 3N HCl (100 mL) was heated on a steam bath for 1 hour. The mixture was cooled, basified with 5N NaOH, extracted with CHCl₃ (3×100 mL) and the combined organic layers were dried over Na₂SO₄ and concentrated in vacuo. The residue was purified by column chromatography on silica eluting with ether (100%), then 5% isopropylamine / ether; followed by a second silica column eluting with 1% isopropylamine / ether to afford 0.80 g of the desired product, m.p. 133°–135° C.

(c)

N-[[1-[[2-(Diethylamino)ethyl]amino]-9-oxothioxanthen-4-yl]methyl]-N-phenylmethanesulfonamide (I: $R^1=R^2=Et$; $Q=CH_2N$ (Ph) $SO_2Me$; $R^8=H$; n=2)

Following a procedure similar to that described in Example 22 it is contemplated that there can be prepared N-[[1-[[2-(diethylamino)ethyl]amino]-9-oxothioxanthen-4 -yl]methyl]-N-phenylmethanesulfonamide from 1-[[2-(diethylamino)ethyl]amino]-4-[(phenylamino)methyl]thioxanthen-9-one of Example 45(b), methanesulfonyl chloride, methylene chloride and triethylamine.

It is contemplated that other members of the genus I may be made in a fashion analogous to that of Examples 1–14, substituting the appropriate 1-[[2-(dialkylamino)ethyl]amino]- or 1-[[3-(dialkylamino) propyl]amino]-9-oxothioxanthen-4-carboxaldehyde for 1-[[2-(diethylamino)ethyl]amino]-9-oxothioxanthen-4-carboxaldehyde, or in a fashion analogous to that of Examples 15–45 but utilizing an appropriate 1-[[(dialkylamino) alkyl]amino]-9-oxothioxanthen-4-carboxaldehyde.

Many of the aldehydes and their precursors are described in U.S. Pat. No. 3,294,803, which is incorporated herein by reference.

Representative examples of the invention were tested for antitumor activity in mice according to the following procedure:

The animals were pooled, implanted subcutaneously with 30 to 60 mg tumor fragments by]2-gauge trocar, and again pooled before unselective distribution to the various treatment and control groups. For early-stage treatment, chemotherapy was started within 1 to 5 days after tumor implantation while the number of cells was relatively small ($10^7$ to $10^8$ cells). For advanced-stage treatment, chemotherapy was delayed until the tumor became relatively large (200 to 300 mg in size). A 300-mg tumor contains approximately $3\times10^8$ total cells. Tumors within a given advanced-stage trial were within a 2.5-fold size range for 90% of the animals. Tumors were measured with a caliper weekly (or twice weekly for the more rapidly growing tumors). Mice were sacrificed when their tumors reached 1500 mg (i.e., before they can cause the animal discomfort). Tumor weights were estimated from two-dimensional measurements.

The treatment and control groups were measured when the control group tumors reached approximately 700 to 1200 mg in size (Median of Group). The median tumor weight of each group was determined (including zeros). The T/C value (weight of treated tumors over the weight of control tumors ) in percent is an indication of antitumor effectiveness: A T/C equal to or less than 42% is considered significant antitumor activity by the Drug Evaluation Branch of the Division of Cancer Treatment (NCI). A T/C value <10% is considered to indicate highly significant antitumor activity. A body weight loss nadir (mean of group) of greater than 20% or greater than 20% drug-deaths is considered to indicate an excessively toxic dosage.

The results are shown in Table I for pancreatic ductal adenocarcinoma #03 and in Table 2 for colon adenocarcinoma #38.

TABLE 1

| Example # | T/C (%) | Weight Loss (g)* | Drug Deaths | Total Dose (mg/kg) i.v. or p.o. |
|---|---|---|---|---|
| 1 | 0 | 1.6 | 0 | 1739 |
| 2 | 0 | 2.0 | 0 | 576 |
| 3 | 7 | 1.6 | 0 | 144 |
| 4 | 0 | 0.4 | 0 | 570 |
| 5 | 0 | 1.6 | 0 | 222 |
| 6 | 0 | 1.6 | 0 | 124 |
| 7 | 0 | 3.2 | 1/5 | 400 |
| 8 | 0 | 0.8 | 0 | 304 |
| 9 | 8 | 1.6 | 0 | 1395 |
| 10 | 0 | 2.4 | 0 | 540 |
| 11 | 0 | 0.8 | 0 | 855 |
| 12 | 36 | 3.2 | 0 | 1298 |
| 13 | 0 | 2.4 | 0 | 431 |
| 14 | 0 | 1.2 | 0 | 448 |
| 15 | 0 | 2.0 | 0 | 390 |

TABLE 1-continued

| Example # | T/C (%) | Weight Loss (g)* | Drug Deaths | Total Dose (mg/kg) i.v. or p.o. |
|---|---|---|---|---|
| 16(a) | 21 | +0.8 | 0 | 1171 |
| 17(f) | 17 | 2.0 | 0 | 1060 |
| 18(e) | 82 | 1.0 | 0 | 128 |
| 18(f) | 0 | 5.2 | 2/5 | 256 |
| 19(e) | 4 | 3.4 | 0 | 610 |
| 20(b) | 10 | 0.4 | 0 | 383 |
| 21(c) | 0 | 4.5 | 0 | 208 |
| 22 | 0 | 3.2 | 0 | 465 |
| 23 | 20 | 2.4 | 0 | 1212 |
| 24 | 0 | 2.3 | 0 | 203 |
| 25 | 0 | 4.6 | 0 | 288 |
| 26 | 13 | 2.2 | 0 | 654 |
| 27 | 5 | +0.8 | 0 | 2594 |
| 28 | 0 | 2.8 | 0 | 552 |
| 29 | 6 | 2.4 | 0 | 2403 |
| 31(c) | 0 | 5.6 | 0 | 248 |
| 30(h) | 0 | 1.4 | 0 | 880 |
| 33 | 28 | 2.0 | 0 | 1281 |
| 34 | 0 | 3.6 | 0 | 248 |
| 36 | 0 | 0.4 | 0 | 155 |
| 37 | 7 | 0 | 0 | 32 |

*Average body weight was 25 g.

TABLE 2

| Example # | T/C (%) | Weight Loss (g)* | Drug Deaths | Total Dose (mg/kg) i.v. |
|---|---|---|---|---|
| 2 | 0 | 2.8 | 0 | 600 |
| 5 | 11 | 2.9 | 0 | 960 |
| 6 | 0 | 5.0 | 3/7 | 132 |
| 6 | 4 | 1.7 | 1/7 | 82 |
| 7 | 16 | 0.6 | 0 | 840 |
| 10 | 0 | 4.0 | 0 | 340(b) |
|  | 24 | 2.3 | 0 | 200(b) |
|  | 22 | 0.6 | 0 | 160(b) |
|  | 2 | 4.0 | 2/5 | 740(a) |
|  | 7 | 1.2 | 0 | 460(a) |
|  | 23 | 2.0 | 0 | 865(b) |
| 11 | 0 | 2.0 | 0 | 1709(a) |
|  | 0 | 0.8 | 0 | 885(a) |
|  | 39 | 0.8 | 0 | 518(b) |
| 16(a) | 20 | 1.2 | 0 | 1000 |
|  | 27 | 1.5 | 0 | 670 |
| 18(e) | 51 | 2.2 | 4/5 | 180 |
|  | 3 | 1.0 | 0 | 120 |
| 25 | 0 | 4.8 | 4/5 | 852(c) |
|  | 0 | 0.6 | 0 | 529(c) |
|  | 0 | 0.8 | 0 | 327(c) |

*Average body weight was 20.5–25.5 g.
(a) = p.o. administration.
(b) = i.p. administration.
(c) = i.v. administration days 3–6 and p.o. administration days 7–10

The compound of Example 5 was tested by intravenous infusion against a number of other tumors as shown in Table 3, and was active at 300 mg/kg p.o. against colon adenocarcinoma #38.

The compound of Example 6 was tested by bolus intravenous injection against a number of other tumors as shown in Table 4.

The compound of Example 8(a) was tested against a number of tumors as shown in Table 5.

The compound of Example 36 was tested against a number of tumors as shown in Table 6.

Representative compounds of the invention were tested against Mammary Adenocarcinoma 16/C/RP as shown in Table 7.

Representative compounds of the invention were tested against P388/adriamycin resistant leukemia as shown in Table 8.

TABLE 3

| Tumor | Total Dosage mg/kg | Schedule | Wt. Loss at Nadir g/mouse | T/C Value in % | Tumor Free | Days of Observation |
|---|---|---|---|---|---|---|
| Human Adeno Squamous Lung #125 | 960 | 16 hr infusion days 7,20 | −0.4 | 16% | 1/4 | 33 |
|  |  |  | −0.4 | 16% | 0/4 | 132 |
|  | 600 |  | −0.4 | 15% | 0/5 | 33 |
|  |  |  | −0.4 | 15% | 0/5 | 132 |
| Mammary 16/C | 720 | 4 hr infusion days 1,4 | −2.0 | 18% | 0/7 | 13 |
|  | 454 |  | −1.2 | 16% | 0/7 | 13 |
| Mammary 16/C/Adr* | 960 | 3 hr infusion days 1,4 | −2.8 | 23% | 0/7 | 27 |
| Colon Adenocarcinoma #38 | 732 | 3–15 bolus | −2.0 | 0% | 1/5 | 100 |
|  | 477 |  | −2.8 | 9% | 0/5 | 100 |
| Colon Adenocarcinoma #38 | 960 | 4 hr infusion days 6,13 | −2.9 | 11% | 2/7 | 20 |
|  |  |  | −2.9 | 11% | 1/7 | 100 |
|  | 600 |  | −2.0 | 26% | 0/3 | 20 |
|  |  |  | −2.0 | 26% | 0/7 | 100 |
| Colon #51 | 720 | 3 hr infusion days 3,7 | −1.1 | 8% | 0/5 | 50 |
|  | 454 |  | −2.8 | 12% | 0/7 | 50 |
| Panc 03 | 222 | 3 hr infusion | −1.6 | 0 | 1/4 | 108 |

*adriamycin resistant

TABLE 4

| Tumor | Total Dosage mg/kg | Schedule | Wt. Loss at Nadir g/mouse | T/C Value in % | Tumor Free | Days of Observation |
|---|---|---|---|---|---|---|
| Colon Adenocarcinoma #38 | 82 | days 6–9 | −1.7 | 1 | 2/7 | 132 |
|  | 51 | bolus | −1.2 | 18 | 1/7 | 132 |
| Mammary 16/C | 82 | days 1–4 | −3.0 | 6 | 0/5 | 23 |
|  | 51 | bolus | −1.2 | 13 | 0/5 | 23 |
| Colon 51/A | 96 | days 3–6,9,11 | −3.0 | 14 | 0/6 | 32 |
|  | 66 | bolus | −2.3 | 28 | 0/6 | 32 |
| Panc 02 | 82 | days 1–4 | −2.0 | 23 | 0/5 | 28 |
|  | 51 | bolus | −1.2 | 42 | 0/5 | 28 |
| Panc 03 | 124 | days 3–4, 6–14 | −1.6 | 0 | 3/5 | 245 |

TABLE 4-continued

| Tumor | Total Dosage mg/kg | Schedule | Wt. Loss at Nadir g/mouse | T/C Value in % | Tumor Free | Days of Observation |
|---|---|---|---|---|---|---|
| | 79 | bolus | −1.0 | 0 | 1/5 | 245 |

TABLE 5

| Tumor | Total Dosage mg/kg | Drug Route | Schedule | Wt. Loss at Nadir g/mouse | T/C Value in % | Drug Deaths | Tumor Free | (Days of Observation) |
|---|---|---|---|---|---|---|---|---|
| Colon Adenocarcinoma #38 | 340 | i.p. | days 3–10 | −2.0 | 0 | 0 | 5/5 | 168 |
| | 196 | i.p. | days 3–10 | −0.0 | 0 | 0 | 1/5 | 168 |
| | 112 | i.p. | days 3–10 | +0.4 | 3 | 0 | — | 168 |
| | 550 | p.o. | days 3–7 | −2.8 | 0 | 0 | 5/5 | 168 |
| | 275 | p.o. | days 3–7 | −0.4 | 0 | 0 | 3/5 | 168 |
| Colon 51/A | 500 | p.o. | days 3–7 | −4.6 | 0 | 4/5 | 0/5 | 31 |
| | 250 | p.o. | days 3–7 | −1.6 | 16 | 0 | 0/5 | 31 |
| Mammary 16/C/Adrl | 340 | i.v. → p.o. | i.v. 2×/day days 1–4; p.o. day 5 | −7.1 | 32 | 5/6 | 0/6 | 22 |
| | 284 | i.v. → p.o. | i.v. 2×/day days 1–4; p.o. days 5–6 | −2.3 | 61 | 3/6 | 0/6 | 22 |
| | 183 | i.v. → p.o. | i.v. 2×/day days 1–4; p.o. days 5–6 | −4.3 | 39 | 0/4 | 0/4 | 22 |

*adriamycin resistant

TABLE 6

| Tumor | Total Dosage mg/kg | Drug Route[a] | Schedule | Wt. Loss at Nadir g/mouse | T/C Value in % | Drug Deaths | Tumor Free | Days of Observation |
|---|---|---|---|---|---|---|---|---|
| Panc 03 | 420 | i.v. | days 3–6 | −5.6 | 0 | 3/5 | 2/5 | 45 |
| | 240 | i.v. | days 3–6 | −0.4 | 0 | 0 | 5/5 | 45 |
| | 155 | i.v. | days 3–6 | −0.4 | 0 | 0 | 5/5 | 45 |
| Colon Adenocarcinoma #38 | 330 | i.v. | days 3–7 | −3.2 | 0 | 0 | 5/5 | 33 |
| | 220 | i.v. | days 3–7 | −0.8 | 0 | 0 | 5/5 | 33 |
| | 147 | i.v. | days 3–7 | 0 | 0 | 0 | 5/5 | 33 |
| Mammary 16/C | 363 | i.v. | days 1–4 | −2.4 | 2 | 2/5 | 2/5 | 21 |
| | 242 | i.v. | days 1–4 | −1.2 | 8 | 1/5 | 0/5 | 21 |
| | 161 | i.v. | days 1–4 | −0.4 | 9 | 0 | 0/5 | 21 |
| Human MX-1 Mammary | 297 | i.v. | days 1–6 | −2.4 | 39 | 0 | 0/5 | 26 |
| | 132 | i.v. | days 1–6 | −0.8 | 27 | 0 | 0/5 | 26 |

[a]Note some injections were changed to p.o. after 2–4 days of injections due to tail vein damage.

TABLE 7

| Example No. | Total Dosage mg/kg | Drug Route | Schedule | Wt. Loss at Nadir g/mouse | T/C Value in % | Drug Deaths | Tumor Free | Days of Observation |
|---|---|---|---|---|---|---|---|---|
| 30(H) | 900 | i.v. infusion | infusion days 1,4 | 0 | 29 | 1/6 | 0/5 | 63 |
| | 600 | i.v. infusion | infusion days 1,4 | −0.7 | 23 | 0/5 | 0/5 | 63 |
| | 400 | i.v. infusion | infusion days 1,4 | −1.0 | 46 | 0/5 | 0/5 | 63 |
| 31(C) | 224 | i.v. | 2×/day, days 3–6 | −4.4 | 0 | 0 | 1/5 | 28 |
| | 156.8 | i.v. | 2×/day, days 3–6 | −1.6 | 5 | 0 | 0/5 | 28 |
| | 109.6 | i.v. | 2×/day, days 3–6 | −1.6 | 6 | 0 | 1/5 | 28 |

TABLE 8

| Example No. | # of P388/Adr cells implanted i.v. on day 0 | Total Dosage mg/kg | Drug Route | Schedule | Wt. Loss at Nadir g/mouse | Drug Deaths | % ILS | Log$_{10}$ Tumor cell kill | Tumor Cell | Days of Observation |
|---|---|---|---|---|---|---|---|---|---|---|
| 10 | 10$^5$ | 520 | i.v. 3 hour infusion | days 1,4 | −3.75 | 3/7 | 54 | 3.5 | 0/7 | 129 |
| | 10$^5$ | 320 | i.v. 3 hour infusion | days 1,4 | −1.75 | 0/5 | 23 | 1.5 | 0/5 | 129 |
| | 10$^5$ | 200 | i.v. 3 hour infusion | days 1,4 | −1.5 | 0/7 | 8 | 0.5 | 0/7 | 129 |
| 13 | 10$^5$ | 450 | i.v. | days 1,4 | −3.0 | 2/7 | 38 | 2.5 | 0/7 | 129 |

TABLE 8-continued

| Example No. | # of P388/Adr cells implanted i.v. on day 0 | Total Dosage mg/kg | Drug Route | Schedule | Wt. Loss at Nadir g/mouse | Drug Deaths | % ILS | Log$_{10}$ Tumor cell kill | Tumor Cell | Days of Observation |
|---|---|---|---|---|---|---|---|---|---|---|
| | $10^5$ | 300 | 3 hour infusion i.v. | days 1,4 | −1.75 | 0/7 | 15 | 1.0 | 0/7 | 129 |
| | $10^5$ | 150 | 3 hour infusion i.v. | days 1,4 | −1.75 | 0/8 | 8 | 0.5 | 0/9 | 129 |
| 30(H) | $10^6$ | 450 | 3 hour infusion i.v. | day 1 | −2.3 | 0/7 | 62 | 5.3 | 0/7 | 43 |
| | $10^6$ | 280 | 3 hour infusion i.v. | day 1 | −1.7 | 0/7 | 69 | 6.0 | 2/7 | 43 |
| 31(C) | $10^6$ | 248 | i.v. → p.o.* | days 1,4 | −3.0 | 1/6 | 0 | 0 | 0/6 | 43 |
| | $10^6$ | 112 | i.v. → p.o.* | days 1,4 | −2.9 | 0/6 | 0 | 0 | 0/6 | 43 |
| 34 | $10^6$ | 320 | i.v. 3.5 hour infusion | day 1 | −3.6 | 5/5 | toxic | LD$_{100}$ | 0/5 | 23 |
| | | 198 | i.v. 3.5 hour infusion | day 1 | −1.2 | 0/5 | 41.7 | 3.3 | 0/5 | 23 |
| | | 123 | i.v. 3.5 hour infusion | day 1 | −1.2 | 0/5 | 8.3 | 0.7 | 0/5 | 23 |
| | | 76 | i.v. 3.5 hour infusion | day 1 | −0.4 | 0/5 | 0 | 0 | 0/5 | 23 |

*p.o. injection day 4 due to tail vein damage.
% ILS = the percentage increase in lifespan.

The pharmaceutical compositions of the present invention include one or more of the compounds of this invention formulated into compositions together with one or more non-toxic physiologically acceptable carriers, adjuvants or vehicles which are collectively referred to herein as carriers, for parenteral injection, for oral administration in solid or liquid form, for rectal or topical administration, and the like.

The compositions can be administered to humans and animals either orally, rectally, parenterally (intravenously, intramuscularly or subcutaneously), intracisternally, intravaginally, intraperitoneally, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

If desired, and for more effective distribution, the compounds can be incorporated into slow release or targeted delivery systems such as polymer matrices, liposomes, and microspheres. They may be sterilized, for example, by filtration through a bacteria-retaining filter, or by incorporating sterilizing agents in the form of sterile solid compositions which can be dissolved in sterile water, or some other sterile injectable medium immediately before use.

Solid dosage forms for oral administration include capsules, tablets, pills, powders and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

The percentage of active component in the composition and method for treating tumors or cancer can be varied so that a suitable dosage is obtained. The dosage administered to a particular patient is variable depending upon the clinician's judgement using as the criteria: the route of administration, the duration of treatment, the size and condition of the patient, the potency of the active component, and the patient's response thereto. An effective dosage amount of active component can thus readily be determined by the clinicjan considering all criteria and utilizing his best judgement on the patient's behalf.

We claim:

1. A compound of formula

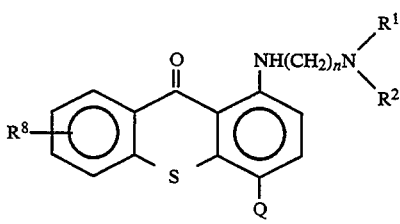

wherein n is 2 or 3;

$R^1$ and $R^2$ are independently lower-alkyl;

Q is a residue chosen from the group consisting of $CH_2NHR^3$, $CH_2NHCHO$, $CH=N-Ar$, $C(O)NR^5R^6$, $CH_2N(R^4)-C(O)R^7$, $CH_2N(C_2H_5)CHO$, $CH_2N(R^4)P(O)$ (O-lower-alkyl)$_2$, $CH_2N=CH-N(R^9)$ ($R^{10}$), $CH_2N(R^4)C(O)CF_3$ and $CH_2N(R^4)C(O)OR^7$;

$R^3$ is hydrogen or lower-alkyl;

$R^4$ is hydrogen, lower-alkyl or Ar;

$R^5$ is hydrogen, lower-alkyl or Ar;

$R^6$ is hydrogen or lower-alkyl;

$R^7$ is lower-alkyl, or Ar;

$R^8$ is hydrogen, lower-alkyl, lower-alkoxy, or hydroxy;

Ar is phenyl or phenyl substituted with methyl, methoxyl, hydroxy, halogen or nitro, and $R^9$ and $R^{10}$ are independently lower-alkyl;

or a pharmaceutically acceptable acid-addition salt or solvate thereof.

2. A compound according to claim 1 wherein:

Q is a residue chosen from the group consisting of $CH_2NHR^3$, $CH_2NHCHO$, $CH=N-Ar$, $C(O)NR^5R^6$, $CH_2N(R^4)-C(O)R^7$, $CH_2N(C_2H_5)CHO$, and $CH_2N(R^4)P(O)$ (O-lower-alkyl)$_2$; and $R^4$ is hydrogen or lower-alkyl.

3. A compound according to claim 2 wherein:

$R^8$ is hydrogen, lower-alkyl, lower-alkoxy or hydroxy; and Ar is phenyl or phenyl substituted with methyl, methoxyl, halogen or nitro.

4. A compound according to claim 3 wherein $R^8$ is hydrogen, lower-alkyl, or lower-alkoxy.

5. A compound according to claim 4 wherein:

Q is a residue chosen from the group consisting of $CH_2NHR^3$, $CH_2NHCHO$, $CH=N-Ar$ and $C(O)NR^5R^6$;

$R^3$ is hydrogen or methyl; and $R^7$ is lower-alkyl.

6. A compound according to claim 5 wherein both of $R^1$ and $R^2$ are methyl or ethyl, and $R^8$ is hydrogen or methoxyl.

7. A compound according to claim 6 wherein n is 2 and both of $R^1$ and $R^2$ are ethyl, and $R^8$ is hydrogen.

8. A compound according to claim 7 wherein Q is $CH=N-Ar$.

9. 1-[[2-(Diethylamino)ethyl]amino]-4-(N-phenylformimidoyl)-thioxanthen-9-one according to claim 8.

10. A compound according to claim 7 wherein Q is $CH_2NHR^3$.

11. 4-(Aminomethyl)-1-[[2-(diethylamino)ethyl]amino]-thioxanthen-9-one according to claim 10.

12. 1-[[2-(Diethylamino)ethyl]amino]-4-[(methylamino)methyl]-thioxanthen-9-one according to claim 10.

13. A compound according to claim 7 wherein Q is $CH_2NHCHO$.

14. N-[[1-[[2-(Diethylamino)ethyl]amino]-9-oxo-thioxanthen-4-yl]methyl]formamide according to claim 13.

15. A compound according to claim 7 wherein Q is $C(O)NR^5R^6$.

16. 1-[[2-(Diethylamino)ethyl]amino]-9-oxothioxanthene-4-carboxamide according to claim 15.

17. A compound according to claim 4 wherein Q is a residue chosen from the group consisting of $CH_2N(R^4)C(O)R^7$, $CH_2N(C_2H_5)CHO$ and $CH_2N(R^4)P(O)(O\text{-lower-alkyl})_2$.

18. A compound according to claim 17 wherein both of $R^1$ and $R^2$ are methyl or ethyl, and $R^8$ is hydrogen or methoxyl.

19. A compound according to claim 18 wherein n is 2 and both of $R^1$ and $R^2$ are ethyl, and $R^8$ is hydrogen.

20. A compound according to claim 19 wherein Q is $CH_2N(R^4)-C(O)R^7$.

21. N-[[1-[[2-(Diethylamino)ethyl]amino]-9-oxothioxanthen-4-yl]methyl]acetamide according to claim 20.

22. N-[[1-[[2-(Diethylamino)ethyl]amino]-9-oxothioxanthen-4-yl]methyl]benzamide according to claim 20.

23. A compound according to claim 19 wherein Q is $CH_2N(C_2H_5)CHO$.

24. N-[[1-[[2-(Diethylamino)ethyl]amino]-9-oxothioxanthen-4-yl]methyl]N-ethylformamide according to claim 23.

25. A compound according to claim 19 wherein Q is $CH_2N(R^4)\text{-}P(O)(O\text{-lower-alkyl})_2$.

26. N-[[1-[[2-(Diethylamino)ethyl]amino]-9-oxothioxanthen-4-yl]methyl]diethyl phosphoramide according to claim 25.

27. A compound according to claim 6 wherein Q is $CH_2NHR^3$.

28. A compound according to claim 27 wherein n is 2 and both of $R^1$ and $R^2$ are ethyl, and $R^8$ is methoxyl.

29. 1-[[2-(Diethylamino)ethyl]amino]-4-[(methylamino)methyl]-7-methoxy-thioxanthen-9-one according to claim 28.

30. A compound according to claim 1 wherein Q is a residue chosen from the group consisting of $CH_2N=CH-N(R^9)$ ($R^{10}$), $CH_2N(R^4)C(O)CF_3$, and $CH_2N(R^4)C(O)OR^7$.

31. A compound according to claim 30 wherein $R^8$ is hydrogen, lower-alkyl, or lower-alkoxy; $R^4$ is hydrogen and Ar is phenyl or phenyl substituted with methyl, methoxyl, halogen, or nitro.

32. A compound according to claim 31 wherein n is 2 and both of $R^1$ and $R^2$ are ethyl and $R^8$ is hydrogen or methoxyl.

33. A compound according to claim 32 wherein Q is $CH_2N=CH-N(R^9)$ ($R^{10}$) and $R^9$ and $R^{10}$ are both methyl.

34. A compound according to claim 32 wherein Q is $CH_2NHC(O)OR^7$.

35. A compound according to claim 34 wherein $R^7$ is lower-alkyl.

36. Methyl N-[[1-[[2-(diethylamino)ethyl]amino]-9-oxothioxanthen-4-yl]methyl]carbamate according to claim 35.

37. Methyl N-[[1-[[2-(diethylamino)ethyl]amino]-7-methoxy-9-oxothioxanthen-4-yl]methyl]carbamate according to claim 35.

38. A pharmaceutical composition which comprises a compound of claim 1 and a pharmaceutically acceptable carrier or diluent.

39. A pharmaceutical composition which comprises a compound of claim 4 and a pharmaceutically acceptable carrier or diluent.

40. A pharmaceutical composition which comprises a compound of claim 12 and a pharmaceutically acceptable carrier or diluent.

41. A pharmaceutical composition which comprises a compound of claim 30 and a pharmaceutically acceptable carrier or diluent.

42. A pharmaceutical composition which comprises a compound of claim 36 and a pharmaceutically acceptable carrier or diluent 43. A pharmaceutical composition which comprises a compound of claim 37 and a pharmaceutically acceptable carrier or diluent.

44. A method for treating a susceptible tumor in a mammal which comprises administering to said mammal an amount of a compound of claim 1 effective to reduce the size of said tumor.

45. A method for treating a susceptible tumor in a mammal which comprises administering to said mammal an amount of a compound of claim 4 effective to reduce the size of said tumor.

46. A method for treating a susceptible tumor in a mammal which comprises administering to said mammal an amount of a compound of claim 12 effective to reduce the size of said tumor.

47. A method for treating a susceptible tumor in a mammal which comprises administering to said mammal an amount of a compound of claim 30 effective to reduce the size of said tumor.

48. A method for treating a susceptible tumor in a mammal which comprises administering to said mammal an amount of a compound of claim 36 ineffective to reduce the size of said tumor.

49. A method for treating a susceptible tumor in a mammal which comprises administering to said mammal an amount of a compound of claim 37 effective to reduce the size of said tumor.

50. A method for treating a susceptible cancer in a mammal which comprises administering to a mammal suffering from said cancer a tumor size-reducing amount of a composition according to claim 38.

51. A method for treating a susceptible cancer in a mammal which comprises administering to a mammal suffering from said cancer a tumor size-reducing amount of a composition according to claim 39.

52. A method for treating a susceptible cancer in a mammal which comprises administering to a mammal suffering from said cancer a tumor-size-reducing amount of a composition according to claim 40.

53. A method for treating a susceptible cancer in a mammal which comprises administering to a mammal suffering from said cancer a tumor size-reducing amount of a composition according to claim 41.

54. A method for treating a susceptible cancer in a mammal which comprises administering to a mammal suffering from said cancer a tumor size-reducing amount of a composition according to claim 42.

55. A method for treating a susceptible cancer in a mammal which comprises administering to a mammal suffering from said cancer a tumor size-reducing amount of a composition according to claim 43.

* * * * *

UNITED STATES PATENT AND TRADEMARK OFFICE
CERTIFICATE OF CORRECTION

PATENT NO. : 5,380,749
DATED : January 10, 1995
INVENTOR(S) : Theodore C. Miller, et. al.

It is certified that error appears in the above-indentified patent and that said Letters Patent is hereby corrected as shown below:

Column 1, after line 13, the following should be inserted--This invention was made with government support under Research Grant No. CA-45962 awarded by the National Institute of Health. The government has certain rights in the invention--.

Signed and Sealed this

Twentieth Day of June, 1995

Attest:

BRUCE LEHMAN

Attesting Officer

Commissioner of Patents and Trademarks